United States Patent
Saffie-Siebert et al.

(10) Patent No.: US 12,207,653 B2
(45) Date of Patent: Jan. 28, 2025

(54) CARRIER SYSTEM FOR PREPARING HERBACEOUS EXTRACTS

(71) Applicant: SISAF LIMITED, Guildford (GB)

(72) Inventors: Roghieh Suzanne Saffie-Siebert, Guildford (GB); Flavia Maria Sutera, Guildford (GB)

(73) Assignee: SISAF LIMITED, Guildford (GB)

( * ) Notice: Subject to any disclaimer, the term of this patent is extended or adjusted under 35 U.S.C. 154(b) by 305 days.

(21) Appl. No.: 17/598,536

(22) PCT Filed: Mar. 30, 2020

(86) PCT No.: PCT/GB2020/050851
§ 371 (c)(1),
(2) Date: Sep. 27, 2021

(87) PCT Pub. No.: WO2020/193997
PCT Pub. Date: Oct. 1, 2020

(65) Prior Publication Data
US 2022/0174952 A1    Jun. 9, 2022

(30) Foreign Application Priority Data
Mar. 28, 2019    (GB) .................................... 1904334

(51) Int. Cl.
| A01N 43/16 | (2006.01) |
| A01N 25/04 | (2006.01) |
| A01N 25/22 | (2006.01) |
| A01N 65/08 | (2009.01) |
| A01N 65/12 | (2009.01) |
| A01N 65/36 | (2009.01) |
| A01P 1/00 | (2006.01) |
| A01P 3/00 | (2006.01) |

(52) U.S. Cl.
CPC ............. *A01N 43/16* (2013.01); *A01N 25/04* (2013.01); *A01N 25/22* (2013.01); *A01N 65/08* (2013.01); *A01N 65/12* (2013.01); *A01N 65/36* (2013.01); *A01P 1/00* (2021.08); *A01P 3/00* (2021.08)

(58) Field of Classification Search
CPC ........ A01N 43/16; A01N 25/04; A01N 25/22; A01N 65/08; A01N 65/12; A01N 65/36; A01P 1/00; A01P 3/00; A61K 8/97; A61K 9/145; A61K 9/143
See application file for complete search history.

(56) References Cited

U.S. PATENT DOCUMENTS

| 5,922,360 A | 7/1999 | Bronder |
| 6,670,335 B2 | 12/2003 | Singh et al. |
| 8,992,984 B1 | 3/2015 | Brinker et al. |
| 9,132,083 B2 * | 9/2015 | Saffie-Siebert ........ A61K 8/553 |
| 9,603,801 B2 * | 3/2017 | Barnett .................. A61K 9/143 |
| 2007/0259013 A1 | 11/2007 | Avram et al. |
| 2009/0053268 A1 | 2/2009 | Depablo et al. |
| 2009/0208556 A1 | 8/2009 | Freeman |
| 2012/0128786 A1 | 5/2012 | Saffie-Siebert |
| 2016/0106091 A1 | 4/2016 | Meunier et al. |
| 2017/0007531 A1 | 1/2017 | Bastos et al. |
| 2018/0296696 A1 | 10/2018 | Ruoslahti |
| 2018/0344641 A1 | 12/2018 | Brinker et al. |

FOREIGN PATENT DOCUMENTS

| AU | 774668 B2 | 4/2001 |
| CA | 3070107 | 1/2019 |
| CN | 104023711 A | 9/2014 |
| CN | 104127886 | 11/2014 |
| CN | 105434205 A | 3/2016 |
| CN | 106 177 982 A | 12/2016 |
| CN | 106265432 A | 1/2017 |
| CN | 107 616 952 A | 1/2018 |
| CN | 107 625 966 A | 1/2018 |
| CN | 107998264 A | 5/2018 |
| CN | 108552223 A | 9/2018 |
| CN | 101296625 A | 10/2018 |
| CN | 106806343 A | 6/2019 |
| EP | 0 272 091 A2 | 6/1988 |
| EP | 2 030 632 A1 | 3/2009 |
| EP | 2459156 | 11/2020 |
| JP | 2006016390 A | 1/2006 |
| JP | 2011032194 A | 2/2011 |
| WO | WO9749375 A1 | 12/1997 |
| WO | WO 02/067998 A1 | 9/2002 |
| WO | WO 2004/016551 A1 | 2/2004 |

(Continued)

OTHER PUBLICATIONS

N.P. Aditya, et al., "Development and evaluation of lipid nanocarriers for quercetin delivery: A comparative study of solid lipid nanoparticles (SLN), nanostructured lipid carriers (NLC), and lipid nanoemulsions (LNE)", LWT—Food Science and Technology, 2014, 59(1), 115-121. (Year: 2014).*

Andreani, T., Kiill, C.P., de Souza, A.L.R. et al., "Effect of cryoprotectants on the reconstitution of silica nanoparticles produced by sol-gel technology", Journal of the Thermal Analysis and Calorimetry, 120, 1001-1007 (2015). (Year: 2015).*

Farman Ali, Asghari Bano and Aliya Fazal, "Recent methods of drought stress tolerance in plants", Plant Growth Regulation (2017) 82:363-375. (Year: 2017).*

Di Ferdinando, Martina, et al. "Flavonoids as antioxidants in plants under abiotic stresses." Abiotic stress responses in plants: metabolism, productivity and sustainability (2012): 159-179. (Year: 2012).*

Elizabeth A. Worrall, Aflaq Hamid, Karishma T. Mody, Neena Mitter and Hanu R. Pappu, "Nanotechnology for Plant Disease Management", Agronomy, 2018, 8, 285, 1-24. (Year: 2018).*

(Continued)

*Primary Examiner* — Mina Haghighatian
*Assistant Examiner* — Nathan W Schlientz
(74) *Attorney, Agent, or Firm* — Charles C. Achkar; Ostrolenk Faber LLP.

(57) ABSTRACT

A method for stabilizing a bioactive herbaceous extract in a composition comprising silicon particles, the method comprising bringing the bioactive herbaceous extract into contact with the silicon particles, in the presence of at least one non-reducing disaccharide. Also related compositions and methods.

18 Claims, 10 Drawing Sheets

(56) References Cited

FOREIGN PATENT DOCUMENTS

| | | |
|---|---|---|
| WO | WO 2006/050221 A2 | 5/2006 |
| WO | WO 2007/012847 A1 | 2/2007 |
| WO | WO2009005963 A2 | 1/2009 |
| WO | WO 2010/038064 A1 | 4/2010 |
| WO | WO2011/001456 | 1/2011 |
| WO | WO 2011/012867 A1 | 2/2011 |
| WO | WO 2013/056132 | 4/2013 |
| WO | WO 2014/165608 | 10/2014 |
| WO | WO 2017/008059 A1 | 1/2017 |
| WO | WO 2017/013250 | 1/2017 |
| WO | WO 2017/041032 | 3/2017 |
| WO | WO 2017/120537 | 7/2017 |
| WO | WO 2017/120537 A1 | 7/2017 |
| WO | WO 2017/181115 A1 | 10/2017 |
| WO | WO2018029247 A1 | 2/2018 |
| WO | WO 2018/134222 | 7/2018 |
| WO | WO 2019/028387 | 2/2019 |

OTHER PUBLICATIONS

Jasmina Kurepa, Timothy E. Shull and Jan A. Smalle, "Quercetin feeding protects plants against oxidative stress", F1000Research, 2016, 5:2430, 1-10. (Year: 2016).*

Roggers R.A. et al., Molecular Pharmaceutics, 2012, vol. 9 "Chemically Reducible Lipid Bilayer Coated Mesoporous Silica Nanoparticles Demonstrating Controlled Release and HeLa and Normal Mouse Liver Cell Biocompatibility and Cellular Internalization", pp. 2770-2777.

Liu D et al., Advanced functional materials, 2013, vol. 23 No 15, "Nanostructured Porous Silicon-Solid Nanocomposite: Towards Enhanced Cytocompatibility and Stability, Reduced Cellular Association, and Prolonged Drug Release", pp. 1893-1902.

Examination report issued in GB Application No. GB1904336.3, mailed Aug. 1, 2019.

Examination report issued in GB Application No. GB1904334.8, mailed Aug. 12, 2019.

Examination report issued in GB Application No. GB1904337.1, mailed Aug. 1, 2019.

Examination report issued in GB Application No. GB1904338.9, mailed Aug. 8, 2019.

Extended European Search Report issued in Application No. 19165904.4, mailed Oct. 14, 2019.

Office Action issued in counterpart Chinese Application No. 202080025659.6 mailed Apr. 17, 2023, English Language translation thereof.

International Search Report issued in International Application No. PCT/GB2020/050850, mailed Jul. 15, 2020.

Written Opinion of the International Searching Authority issued in International Application No. PCT/GB2020/050850, mailed Jul. 15, 2020.

Saffie-Siebert R et al., Drug Discovery World 2005; 6: 71-6.

Saffie-Siebert, R et al., Pharmaceutical Technology Europe, 17(4), 21-28 (2005).

Luo, D., Saltzman, W. M., Gene Therapy (2006) 13, 585-586.

Ahola, M., Kortesuo, P., Kangasniemi, I., Kiesvaara, J., Yli-Urpo, A., Int. J. Pharm. 195 (2000) 219 227.

Ahola. M., Säilynoja, E.S., Raitavuo, M.H., Vaahtio, M.H., Salonen, J.I., Yli-Urpo, A.U.O., Biomat. (2001), 15, 2163-2170.

Lu, J., Liong, M., Zink, J., Tamanoi, F, Small. 2007, 3: 1341-1346.

Studies of the kinetics of the precipitation of uniform silica particles through the hydrolysis and condensation of silicon alkoxides, Journal of Colloid and Interface Science, vol. 142, Issue 1, Mar. 1, 1991, pp. 1-18 G.H Bogush and C.F Zukoski IV.

Communication Pursuant to Article 94 (3) EPC issued in counterpart application No. 20 718 723.8, mailed Jun. 29, 2022.

Juewen Liu et al: "Porous Nanoparticle Supported Lipid Bilayers (Protocells) as Delivery Vehicles", Journal of the American Chemical Society, vol. 131, No. 4, Feb. 4, 2009, pp. 1354-1355, XP055029872, ISSN: 0002-7863, DOI: 10.1021.

International Search Report issued in International Application No. PCT/GB2020/050849, mailed May 20, 2020.

Written Opinion of the International Searching Authority issued in International Application No. PCT/GB2020/050849, mailed May 20, 2020.

International Search Report issued in International Application No. PCT/GB2020/050854, mailed Jul. 7, 2020.

Written Opinion of the International Searching Authority issued in International Application No. PCT/GB2020/050854, mailed Jul. 7, 2020.

Communication Pursuant to Article 94 (3) EPC issued in counterpart application No. 20 716 902.0, mailed Jul. 5, 2022.

Communication Pursuant to Article 94 (3) EPC issued in counterpart application No. 20 718 724.6, mailed Aug. 8, 2022.

Communication Pursuant to Article 94 (3) EPC issued in counterpart application No. 20 718 725.3, mailed Jun. 29, 2022.

International Search Report issued in International Application No. PCT/GB2020/050853, mailed Jul. 10, 2020.

Written Opinion of the International Searching Authority issued in International Application No. PCT/GB2020/050853, mailed Jul. 10, 2020.

Xie W, Hu L. Mesoporous SBA-15 Silica-supported Diisopropylguanidine: an Efficient Solid Catalyst for Interesterification of Soybean Oil with Methyl Octanoate or Methyl Decanoate. J Oleo Sci. Oct. 1, 2016;65(10):803-813. Epub Sep. 15, 2016.

Communication Pursuant to Article 94 (3) EPC issued in counterpart application No. 20 718 722.0, mailed Aug. 8, 2022.

U.S. Appl. No. 17/598,467, filed Sep. 27, 2021, published as US 2022-0183989 A1.

U.S. Appl. No. 17/985,595, filed Sep. 27, 2021, published as US 2022-0151944 A1.

U.S. Appl. No. 17/598,703, filed Sep. 27, 2021.

U.S. Appl. No. 17/599,020, filed Sep. 27, 2021, published as US 2022-0184038 -A1.

Examination Report issued in counterpart European Application No. 20 718 724.6 mailed Jul. 25, 2023 indicating all claims are allowable.

Office Action issued in counterpart Chinese Application No. 202080023934.2 mailed Apr. 21, 2023, English Language translation thereof.

Ruijin Zhao,et al. Beijing: Military Medical Science Press, "Oncology Health Education," Aug. 31, 2010, pp. 530-531.

Zhihua Wu, et al., Guangzhou: Guangdong Science and Technology Press, "Dermatologic Venereology: Textbook Edition," Jun. 30, 2013, p. 284.

Jinglong Cai, et al., Hangzhou: Zhejiang Science and Technology Publishing House, "Scar Plastic and Aesthetic Surgery'" Mar. 31, 2015, p. 786.

Office Action issued in counterpart Chinese Application No. 202080025658.1 mailed Jun. 30, 2023, English Language translation thereof.

Examination Report issued in counterpart European Application No. 20 718 722.0 mailed Jul. 7, 2023.

Yanan Liu, et al., "Effect of mesoporous silica nanoparticles on drug loading properties and drug release of flavonoids." Proprietary Chinese Medicines, Mar. 31, 2015, vol. 38, Issue 3, pp. 528-532.

V.V. Cotea et al., Mesoporous silica SBA-15, a new adsorbent for bioactive polyphenols from red wine Oct. 18, 2011, Analytica Chimica Acta, vol. 732, V.V., pp. 1-26.

Office Action issued in counterpart Chinese Application No. 202080025658.1 mailed Nov. 2, 2022 with English Language translation thereof.

Office Action issued in counterpart Chinese Application No. 202080025724.5 mailed Nov. 2, 2022 with English Language translation thereof.

Office Action issued in counterpart Indian Application No. 202147045961 mailed Apr. 6, 2023.

Office Action issued in counterpart Chinese Application No. 202080025724.5 mailed Mar. 30, 2023, English Language translation thereof.

International Search Report issued in International Application No. PCT/GB2020/050851, mailed May 25, 2020.

(56) References Cited

OTHER PUBLICATIONS

Written Opinion of the International Searching Authority issued in International Application No. PCT/GB2020/050851, mailed May 25, 2020.
Lundstrom et al., Medicines, 2017, 4, 12.
Ramešová et al., Anal. Bioanal. Chem., 2016, 402, 975.
Pluskota A, "In Caenorhabditis elegans Nanoparticle-Bio-Interactions Become Transparent: Silica-Nanoparticles Induce Reproductive Senescenc." PLoS One | www.plosone.org;Aug. 2009 | vol. 4 | Issue 8 | e6622.
Office Action issued in Chinese Application No. 202080024934.2 mailed Oct. 25, 2023, English Language translation thereof.
Model Biotoxicology Based on Summaries and Reflections on Hidradenitis elegans Research, Dayong Wang, et al., Nanjing: Southeast University Press, pp. 153, publication date: Jan. 31, 2013).
Office Action issued in Japanese Application No. JP 2021-557827 mailed Nov. 21, 2023, English Language translation thereof.
Office Action issued in JP Application No. 2021-557824 mailed Jan. 30, 2024, English Language translation thereof.
Pan et al., Colloids and Surfaces B: Biointerfaces 159 (2017) 375-385.
Cheang, Tuck-yun, et al. "Promising plasmid DNA vector based on APTES-modified silicon nanoparticles." International journal of nanomedicine (2012): 1061-1067.).
Office Action issued in Chinese Application No. 202080023934.2 mailed Apr. 21, 2023, English Language translation thereof.

* cited by examiner

US 12,207,653 B2

CARRIER SYSTEM FOR PREPARING HERBACEOUS EXTRACTS

CROSS REFERENCE TO RELATED APPLICATION

The present application is a § 371 National Phase application based on PCT/GB2020/050851 filed Mar. 30, 2020, which claims the benefit of GB Application No. 1904334.8, filed Mar. 28, 2019 the subject matter of each of which is incorporated by reference in their entirety.

FIELD OF THE INVENTION

The present invention concerns delivery agents for containing herbaceous extracts. More particularly, but not exclusively, this invention concerns the use of silicon nanoparticles as stabilization, delivery and controlled release agents. The invention also concerns related compositions and methods.

BACKGROUND OF THE INVENTION

Herbaceous extracts are useful in many applications. For example, they are useful in both traditional and modern medicine, for nutritional purposes and for the treatment of plants, for example to protect them against pathogens.

Developments in the fields of genomics and proteomics have provided new opportunities for more detailed analysis of plant metabolites and related extracts, improving understanding of the function of their individual components, thus opening new perspectives on their usage for treating human and animal disorders as well as increasing plant's defences against microorganisms. [Lundstrom et al., Medicines, 2017, 4, 12]

The use of herbaceous extracts can be problematic in many cases because they often contain chemicals which are unstable in storage and use, especially when formulated into an aqueous environment for administration. This makes it difficult to ensure that an effective dose of useful compounds is maintained and may also result in the formation of toxic degradation products.

For example, both natural flavonoid compounds quercetin (3,3',4',5,7-pentahydroxyflavone) and luteolin (3',4',5,7-tetrahydroxyflavone), extracted from *Sphaeranthus indicus* specimen, are important bioactive molecules able to exert antioxidative, anti-allergic, and anti-inflammatory effects. However, both are unstable when exposed to oxygen or other oxidants, which causes degradation of their chemical moieties. [Ramešová et al., Anal. Bioanal. Chem., 2016, 402, 975].

The mechanism of oxidation of polyphenols and their stability in aqueous environments is governed by oxidation pathways of hydroxy compounds and the distribution of various dissociation forms in solution.

There is a need to stabilize herbaceous extracts, especially those which contain flavonoid compounds and polyphenols and especially those which are formulated into aqueous compositions. The plant kingdom contains many thousands of chemical compounds for various functions including defences against insects, fungi, viruses and bacteria and represents an extremely valuable resource, the potential of which is incompletely exploited due to poor compound stability.

The present invention is based on using silicon-containing particles for stabilizing herbaceous extracts and/or as a carrier for herbaceous extracts. Silicon-containing particles are especially useful because they can provide a hydrophilic environment in which hydrophilic compounds can be stabilized and, thereby, have longer half-lives than when formulated into aqueous compositions because silicon-containing particles provide an environment with which hydrophilic compounds can associate but which can also be associated with hydrophobic lipids it allows microsphere encapsulation technology to be extended into the stabilization of hydrophilic herbaceous compounds.

The use of silicon-containing materials is also advantageous because they are non-toxic. Silicon-containing materials can be produced as micro or nanoparticles and used thus as a stabilization agent which is generally regarded as harmless both to the human body and to the natural environment.

Silicon

Silicon is an essential trace element for plants and animals. Silicon has a structural role as a constituent of the protein-glycosaminoglycan complexes found in the connective tissue matrix of mammals, as well as having a metabolic role in growth and osteogenesis (silicon is involved in the process of bone mineralisation). Thus, silicon is essential for the normal development of bones and connective tissue. Silicon is also known to play an important role in skin health, acting as a collagen and elastin promoter and being involved in antioxidative processes in the body. It is implicated in the production of glycosaminoglycans and silicon-dependent enzymes increase the benefits of natural tissue building processes.

Manipulation of the silicon surface requires consideration. This is because the binding of a drug molecule to the silicon surface is highly dependent on the surface energy. Hydroxylation of the surface will reduce the surface contact angle, favouring the binding of polar molecules. Alternatively, growth of a surface oxide will increase the surface contact angle, favouring the binding of hydrophobic molecules. Consequently, both particle size and surface chemistry should be taken into account to obtain control over the level of active agent loading and rate or release.

The present inventors have developed a method for stabilizing a bioactive herbaceous extract in compositions comprising silicon-containing nanoparticles.

SUMMARY OF THE INVENTION

According to a first aspect of the invention, there is provided a method for stabilizing a bioactive herbaceous extract in a composition comprising silicon particles, the method comprising bringing the bioactive herbaceous extract into contact with the silicon particles, in the presence of at least one non-reducing disaccharide.

The bringing together of the bioactive herbaceous extract and the silicon particle may optionally be in the presence of one or more further compounds, for example amino acids and/or lipid compounds.

According to a second aspect of the invention, there is provided a composition comprising the silicon particles prepared according to the first aspect of the invention, and, optionally, one or more further ingredients.

According to a third aspect of the invention, there is provided silicon particles prepared according to the first aspect of the invention or a composition according to the second aspect of the invention for use as a medicament.

According to a fourth aspect of the invention, there is provided a method for treating a medical condition comprising administering an effective dose of one or more bioactive herbaceous extracts to a subject in need thereof, wherein the one or more bioactive herbaceous extracts are administered as a composition according to an embodiment of the second aspect of the invention.

According to a fifth aspect of the invention there is provided a method for providing a cosmetic benefit to a subject comprising administering to said subject a composition according to an embodiment of the second aspect of the invention.

According to a sixth aspect of the invention, there is provided a method of protecting a plant comprising administering to said plant a composition according to an embodiment of the second aspect of the invention wherein the bioactive herbaceous extract comprises one or more plant protection compound(s).

It will, of course, be appreciated that features described in relation to one aspect of the present invention may be incorporated into other aspects of the present invention. For example, methods of the invention may incorporate any of the features described with reference to compositions and other products of the invention and vice versa.

DETAILED DESCRIPTION

Figure 1:
FIG. 1. Photograph showing first 4 tubes—*Sphaeranthus indicus* herbaceous extract dispersed in respectively: ethanol, distilled $H_2O$, methanol and chloroform. As noticeable from observing the bottom part of the tubes, an insoluble sediment is visible after dispersing the herbaceous extract in the solvents. In tubes 5 to 8 there is shown respectively: *Sphaeranthus indicus* herbaceous extract dispersed in distilled $H_2O$, then filtered; solution obtained after cold extraction in $H_2O$ and diluted 1:10; solution obtained after hot extraction in $H_2O$ (75° C.) and diluted 1:10; solution obtained after hot extraction in $H_2O$ (75° C.).
Figure 2:
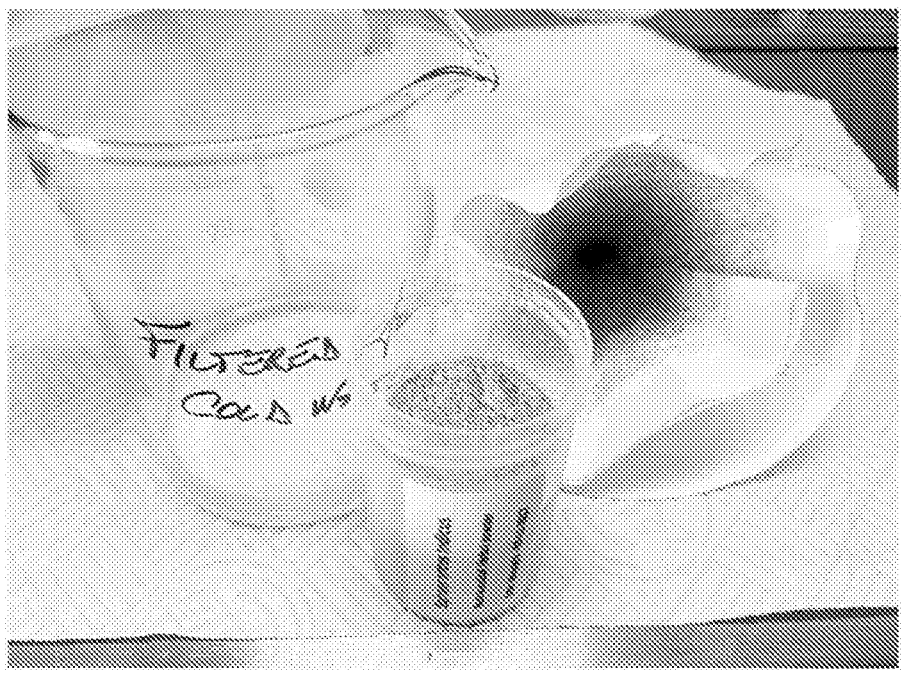
FIG. 2. Photograph showing the appearance of the filtered solution of *Sphaeranthus indicus* following hot water (75° C.) extraction, *Sphaeranthus indicus* herbal powder, and filter paper after filtration.

According to a first aspect of the invention, there is provided a method for stabilizing a bioactive herbaceous extract (for example, one or more of a *Sphaeranthus indicus* extract, such as an extract comprising quercetin, a *cannabis* plant extract, such as an extract comprising one or more cannabinoids, an olive tree extract, or a citrus tree extract) in a composition comprising silicon particles, the method comprising bringing the bioactive herbaceous extract into contact with the silicon particles in the presence of at least one non-reducing disaccharide (for example, trehalose or a mixture comprising trehalose).

Silicon Particles

According to all aspects of the invention, the composition comprises silicon particles. In some embodiments (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) they are silicon nanoparticles having a nominal diameter of between 20 and 400 nm, for example 50 to 350 nm, for example 80 to 310 nm, for example 100 to 250 nm, for example 120 to 240 nm, for example 150 to 220 nm, for example about 200 nm. In other embodiments (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) they are silicon microparticles having a nominal diameter of between 0.2 and 40 mm, for example 0.5 mm to 35 mm, for example 0.8 mm to 31 mm for example 1 mm to 25 mm, for example 1.2 mm to 22 mm, for example 2 mm to 15 mm, for example 5 mm to 10 mm. The nominal diameter referred to above, may refer to the mean diameter and at least 90% of total particles in a sample of silicon nanoparticles may fall within the size range specified. They are preferably porous. They are made of either pure silicon or a hydrolysable silicon-containing material. Silicon particles can be made porous by standard techniques such as contacting the particles with a hydrofluoric acid (HF)/ethanol mixture and applying a current. By varying the HF concentration and the current density and time of exposure, the density of pores and their size can be controlled and can be monitored by scanning electron micrography and/or nitrogen adsorption desorption volumetric isothermic measurement.

The silicon particles may be pure silicon or another silicon-containing material. In some embodiments (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) if they are not pure silicon, they preferably contain at least 50, 60, 70, 80, 90 or 95% silicon and preferably show a rate of hydrolysis (for example in PBS buffer at room temperature) of at least 10% of the rate of hydrolysis of pure silicon particles of the same dimensions. Assays for hydrolysis of silicon-containing material are widely known in the art, for example as described in WO2011/001456.

Particles according to all aspects of the invention are preferably porous. For example, their porosity may increase their surface area by a factor of at least 1.5, 2, 2.5, 3, 3.5 or 4 over the surface area of an equivalently sized non-porous material. In some embodiments (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) their total surface area is preferably increased by virtue of their porosity by at least 50% or at least 100% over the surface area of a corresponding non-porous particle. In many circumstances porous silicon particles will in reality have a much greater increase in total surface area by virtue of their porosity.

In some embodiments (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the silicon particles have an average diameter of between 20-300 nm, from example between 20-290 nm, between 20-280 nm, between 20-270 nm, between 20-260 nm, between 20-250 nm, between 20-240 nm, between 20-230 nm, between 20-220 nm, between 20-210 nm, especially between 20-200 nm. For some applications relating to dermal application, it is advantageous that the silicon nanoparticles are sized so as to be too small to block pilosebaceous ostra or sweat ducts (pores), but to allows the particles to actively penetrate to the bottom of the hair follicles rather than merely acting as a surface reservoir for the bioactive herbaceous extract.

Non-Reducing Disaccharide

According to all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract) there is included in the relevant product or method at least one non-reducing disaccharide. The non-reducing disaccharide may optionally be selected from sucrose, trehalose, raffinose, stachyose and verbascose or mixtures of any thereof, most preferably the non-reducing disaccharide is trehalose, or a mixture comprising trehalose.

Ratio of Non-Reducing Disaccharide to Silicon

Preferably, the non-reducing disaccharide (for example, trehalose or a mixture comprising trehalose) is present at a weight ratio to silicon of at least 1:1000, at least 1:100, at least 1:50, at least 1:10, at least 1:1, or at least 1:0.5. Preferably, the non-reducing disaccharide is trehalose optionally present at such a weight ratio.

Amino Acids

According to certain embodiments of all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the silicon particles are further contacted with an amino acid (for example, one or both of arginine and glycine). In its broadest sense, the term "amino acid" encompasses any artificial or naturally occurring organic compound containing an amine ($-NH_2$) and carboxyl ($-COOH$) functional group. It includes an $\alpha$, $\beta$, $\gamma$ and $\delta$ amino acid. It includes an amino acid in any chiral configuration. According to some embodiments, it is preferred to be a naturally occurring $\alpha$-amino acid. It may be a proteinogenic amino acid or a non-proteinogenic (such as carnitine, levothyroxine, hydroxyproline, ornithine or citrulline) naturally-occurring amino acid. It is especially preferred to comprise arginine, histidine, or glycine, or a mixture of arginine and glycine.

Accordingly, pharmaceutically- or cosmetically-compatible compositions of the invention are such that the surface contacted particles are associated with the bioactive herbaceous extract, which is an active pharmaceutical or cosmetic agent (for example, a *Sphaeranthus indicus* extract, such as an extract comprising quercetin, a *cannabis* plant extract, such as an extract comprising one or more cannabinoids, an olive tree extract, or a citrus tree extract) and an amino acid (preferably selected from arginine, glycine, histidine and mixtures thereof, most preferably both arginine and glycine).

According to preferred embodiments (for example, when the non-reducing disaccharide is trehalose or a mixture comprising trehalose) at least 80%, for example at least 90% of the bioactive herbaceous extract (for example, a *Sphaeranthus indicus* extract, such as an extract comprising quercetin, a *cannabis* plant extract, such as an extract comprising one or more cannabinoids, an olive tree extract, or a citrus tree extract) by weight present in the products of all aspects of the invention is associated with the silicon particles. Optionally, an amino acid is provided, for example one or both of arginine and glycine.

Molecular association between a bioactive herbaceous extract (for example, a *Sphaeranthus indicus* extract, such as an extract comprising quercetin, a *cannabis* plant extract, such as an extract comprising one or more cannabinoids, an olive tree extract, or a citrus tree extract) and the silicon particle advantageously ensures that the bioactive herbaceous extract becomes bio-available and is released in a controlled manner. The rate of release can be controlled in order to avoid dose-dumping and/or to ensure release only when the particles have found their way to their intended location.

Using an amino acid (for example, one or both of arginine and glycine) in addition to a disaccharide (for example, trehalose or a mixture comprising trehalose) has been found to provide a beneficial stabilising effect on a bioactive herbaceous extract loaded onto the silicon particles (for example, a *Sphaeranthus indicus* extract, such as an extract comprising quercetin, a *cannabis* plant extract, such as an extract comprising one or more cannabinoids, an olive tree extract, or a citrus tree extract). In particular, use of an amino acid and a disaccharide has be shown to stabilise the bioactive herbaceous extract in biological fluids or the outdoor environment.

According to certain embodiments of all aspects of the invention, the disaccharide-contacted silicon particles (for example, silicon particles contacted with trehalose or a mixture comprising trehalose) are further contacted with arginine. The surface treatment of silicon particles with arginine prior to being loaded with a bioactive herbaceous extract (for example, a *Sphaeranthus indicus* extract, such as an extract comprising quercetin, a *cannabis* plant extract, such as an extract comprising one or more cannabinoids, an olive tree extract, or a citrus tree extract) demonstrated better stability of the extract in biological fluids than particles without the arginine pre-treatment.

Ratio of Amino Acid to Silicon

Preferably, the weight ratio of amino acid (for example, one or both of arginine and glycine) to silicon is between 0.05:1 and 2:1, for example between 0.05:1 and 1.8:1, 0.05:1 and 1.6:1, 0.05:1 and 1.4:1, 0.05:1 and 1.2:1, 0.05:1 and 1:1, 0.05:1 and 0.9:1, 0.05:1 and 0.8:1, 0.05:1 and 0.6:1, 0.05:1 and 0.5:1, 0.05:1 and 0.4:1, 0.05:1 and 0.3:1, 0.05:1 and 0.2:1, preferably between 0.2:1 and 0.8:1, especially between 0.3:1 and 0.7:1 by mass. Advantageously, this ratio of amino acid to silicon further affects the rate of release of, and stabilise a bioactive herbaceous extract (for example, a *Sphaeranthus indicus* extract, such as an extract comprising quercetin, a *cannabis* plant extract, such as an extract comprising one or more cannabinoids, an olive tree extract, or a citrus tree extract) conveyed by the silicon particle.

According to all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the amino acid may be any amino acid. Preferably, the amino acid is arginine or glycine or a combination of glycine and arginine. In some embodiments, the amino acid is a combination of arginine and glycine, wherein the ratio of Arg:Gly is between 1:0.6 and 3:1, for example between 1:0.8 and 2.5:1, for example between 1:1 to 2:1 by mass.

According to some embodiments of all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the disaccharide-contacted silicon particles are also contacted with arginine. Preferably, the ratio of arginine to silicon is between 0.05:1 to 0.4:1, for example between 0.08:1 and 0.35:1, especially 0.09:1 to 0.32:1 by mass. Advantageously, such ratios have been found to provide a high rate of release of bioactive herbaceous extract.

Arginine present at ratios lower than 0.2:1 (Arg:Si) is not effective in enhancing the release of the bioactive herbaceous extract. Nevertheless, even in these low amounts, arginine contributes to the stability of the bioactive herbaceous extract (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract).

According to certain embodiments of all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the disaccharide-contacted particles are further contacted with histidine. Advantageously, an enhanced bioactive herbaceous extract stability is observed for histidine when used in combination with non-reducing disaccharide (for example, trehalose or a mixture comprising trehalose). This could be attributable to a better buffering effect in the range pH 5.12 to pH 7.12, for the resultant composition. Preferably, the ratio of histidine to silicon is between 0.05:1 to 0.4:1, for example between 0.08:1 and 0.5:1, especially 0.35:1 to 0.45:1 by mass. Histidine may be present in the absence of arginine and/or glycine, or histidine may be present in addition to arginine or glycine or mixtures thereof.

Advantageously, this ratio allows for a high rate of bioactive herbaceous extract release (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract).

According to certain embodiments of all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the disaccharide-contacted particles are further contacted with glycine. Advantageously, glycine facilitates cytoplasmic permeation of the silicon particles within animal or human cells. A high ratio of glycine to silicon favored an increased rate of release of the bioactive herbaceous extract.

According to other embodiments of all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract; and/or the non-reducing disaccharide is trehalose or a mixture comprising trehalose) the silicon particle is further contacted with glycine. Advantageously, such compositions enable bioactive herbaceous extract release to reach a plateau over time. In particular a controlled release of the bioactive herbaceous extract may be provided over a 12 hour period.

In some embodiments of the second aspect of the invention, there is provided a composition comprising silicon particles contacted with at least one non-reducing disaccharide (for example, trehalose or a mixture comprising trehalose) and optionally at least one amino acid (for example, one or both of arginine and glycine) for use as a delivery system for prolonged drug release over time. The composition is preferably an aqueous composition or a water/oil emulsion or an aqueous gel. The composition may, for example, be an aqueous cream, an injectable suspension, a hydrogel or a patch.

Oils

In certain embodiments of all aspects of the invention (for example, when the bioactive herbaceous extract is a *Sphaeranthus indicus* extract, such as an extract comprising quercetin, a *cannabis* plant extract, such as an extract comprising one or more cannabinoids, an olive tree extract, or a citrus tree extract, and/or the non-reducing disaccharide is trehalose or a mixture comprising trehalose) the composition further comprises at least one oil. Advantageously, the inclusion of oils into the composition of the invention provides beneficial effects of odor masking, an enhanced observed permeation/penetration rate of the bioactive herbaceous extract (for example across skin or into plant tissue), and formation of an amphiphilic interface able to overcome precipitation due to a poor solubility at an oil/water interface.

In preferred embodiments, the oils are selected from limonene, coconut oil, oregano oil, sesame oil, flaxseed oil or combinations thereof.

In certain embodiments, the oils are selected from limonene, coconut oil or a combination thereof. Advantageously, the use of such oils has been demonstrated to be effective at masking odors such as fish oils (for example, omega 3 fish oil).

In certain embodiments, the oils are selected from limonene, oregano oil, sesame oil or a combination thereof. Preferably, the composition comprises oregano and sesame oil. Advantageously, these oils have been demonstrated to facilitate the loading, vehiculating and delivery of a bioactive herbaceous extract (for example, a hydrophobic bioactive herbaceous extract). In certain embodiments the mass ratio of silicon particle:oregano oil:sesame oil is 1.6:4.5:3.8.

In another embodiment of all aspects of the invention, the oil is limonene. Advantageously, the inclusion of limonene in the composition has been shown to enhance the rate of skin permeation of a bioactive herbaceous extract (for example, a hydrophobic bioactive herbaceous extract) loaded onto the silicon particles, when compared to silicon particles without the additional oil component. In particular, the embodiments of the second aspect of the invention that further comprise oils have been found to improve the amphiphilic nature of the particles to overcome the poor water in oil distribution of the loaded silicon particles. This is especially true when the bioactive herbaceous extract is a hydrophobic peptide.

According to certain embodiments of the invention (for example, when the herbaceous extract is a hydrophobic herbaceous extract) the at least one oil is present in the composition at levels of at least 1, 5, 10, 20, 30 or 40% by weight, or up to 1, 5, 10, 20, 30 or 40% by weight.

Bioactive Herbaceous Extract

According to preferred embodiments of all aspects of the invention (for example, when the non-reducing disaccharide is trehalose or a mixture comprising trehalose; optionally in such examples, one or more amino acids are provided, such as one or more of glycine and arginine) the bioactive herbaceous extract is one or more compounds extracted from plant material, for example from roots, stems, bark, leaves, seeds, fruit or flowers. It may be a raw extract or may be purified to an appropriate degree. It is one or more organic compounds according to certain preferred embodiments. At least one of those organic compounds (preferably the organic compound which predominates on a molar basis) is selected from compounds which are phenols, diphenols or polyphenols. They may preferably be flavonoids, flavonols, isoflavonoids, neoflavonoids, flavones.

According to certain embodiments (for example, when the non-reducing disaccharide is trehalose or a mixture comprising trehalose; optionally in such examples, one or more amino acids are provided, such as one or more of glycine and arginine) the bioactive herbaceous extract in accordance with all aspects of the invention preferably comprises a compound selected from a phenol, a diphenol or a polyphenol.

According to certain embodiments (for example, when the non-reducing disaccharide is trehalose or a mixture comprising trehalose; optionally in such examples, one or more amino acids are provided, such as one or more of glycine and arginine) the phenol may be a cannabinoid, capsaicin, cavaciol, a phytoestergen, eugenol, gallic acid, gualacol, methylsalicylate, 4-(4-hydroxyphenyl)butan-2-one (raspberry ketone), calicylic acid, aspirin, thymol or sesamol.

Alternatively, in some embodiments (for example, when the non-reducing disaccharide is trehalose or a mixture comprising trehalose; optionally in such examples, one or more amino acids are provided, such as one or more of glycine and arginine) the bioactive herbaceous extract may be a terpene (for example a hemiterpene such as a prenol or 3-methylbutanoic acid); a monoterpene such as geraniol, terpineol, limonene, myrcene, linalool or pinene; an irridoid such as auubuin or catapol; a sesquiterpene such as humulene, farnesol, farnesene, cadinene, caryophyllene, vetivazulene, guaiazulene, lingifolene, copanene, patchulol; a diterpene such as geranylgeranylpyrophosphate, cafestol, kahweol, cembrene, taxadiene, taxol, retinol, retinal or phytol; a sesterterpene; a triterpene; a steroid, a tetraterpene such as lycopene, or a carotene; or a norisoprenoid such as 3-oxo-oxionol, 7,8-dihydroionone, megastigmane-3,9-diol or 3-oxo-7,8-dihydro-α-ionol).

Alternatively, in some embodiments (for example, when the non-reducing disaccharide is trehalose or a mixture comprising trehalose; optionally in such examples, one or more amino acids are provided, such as one or more of glycine and arginine) the bioactive herbaceous extract may be a flavonoid (for example a flavone such as apigenin, luteolin, tangeritin, chrysin, 6-hydroxyflavone, 7,8-dihydroxyflavone, baicalein, scutellarein or wogonin; a flavonol such as quercetin, kaempferol, myricetin, isorhamnetin and glycosylated forms thereof; a flavanone glycosides such as eriodictyol, hesperetin, hesperidin, poncirin, sakuranetin, sakuranin, sterubin, pinostrobin, homioeriodictyol, isosacuranetin, naringenin, naringin, pinocembrin; a flavanol such as catechin, epicatechingallate, epigollocatechin, epicallocatechin gallate; proanthocyanidins; theaflavins; thearubigins; anthocyanins such as aerantinidin, cyanidin, peonidin, petunidin, delphinidin.

In some embodiments (for example, when the non-reducing disaccharide is trehalose or a mixture comprising trehalose; optionally in such examples, one or more amino acids are provided, such as one or more of glycine and arginine) the bioactive herbaceous extract may be a herbaceous extract, such as an olive tree extract, a citrus tree extract, a *Sphaeranthus indicus* plant extract, or a *cannabis* plant extract. The bioactive herbaceous extract may be or may comprise quercetin. For example, the bioactive herbaceous extract may be a *Sphaeranthus indicus* plant extract comprising quercetin.

In some embodiments (for example, when the non-reducing disaccharide is trehalose or a mixture comprising trehalose; optionally in such examples, one or more amino acids are provided, such as one or more of glycine and arginine) the bioactive herbaceous extract may comprise one or more cannabinoids, such as one or more of cannabidiol, tetrahydrocannabinol, and cannabigerol. The bioactive herbaceous extract may comprise one or more cannabinoids such as one or more of tetrahydrocannabinol, tetrahydrocannabinolic acid, cannabidiol, cannabidiolic acid, cannabinol, cannabigerol, cannabichromene, cannabicyclol, cannabivarin, tetrahydrocannabivarin, cannabidivarin, cannabichromevarin, cannabigerovarin, cannabigerol monomethyl ether, cannabielsoin and cannabicitran.

In some embodiments (for example, when the non-reducing disaccharide is trehalose or a mixture comprising trehalose; optionally in such examples, one or more amino acids are provided, such as one or more of glycine and arginine) the bioactive herbaceous extract may be taxol, curcumin, aloe-emodin, glycyrrhizin, kojic acid, *Lupinus aldus* extract or a plant such as leberine, morphine, quinin, ephedrine, homoharringtonine, galantamine, vincamine, quinidine, chelerythrine or piperine. Specific compounds may include:

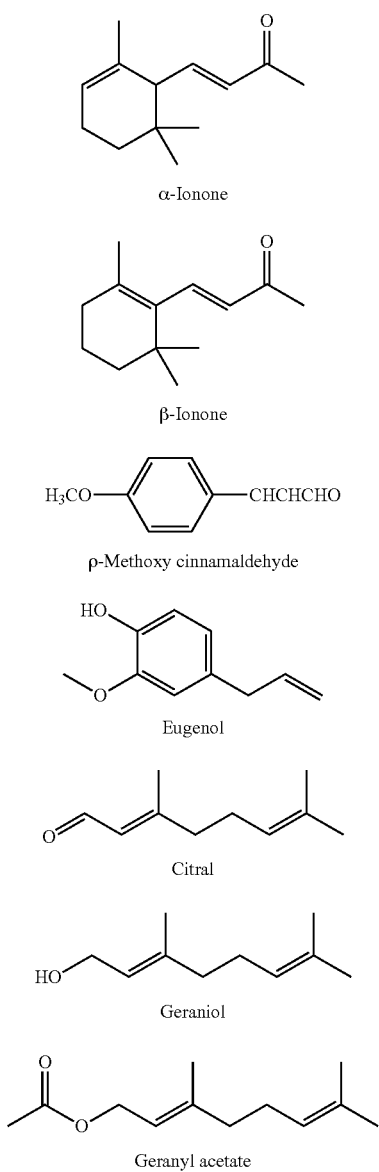

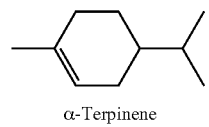

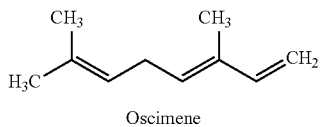

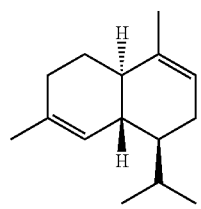

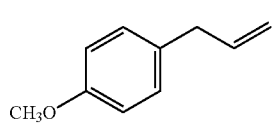

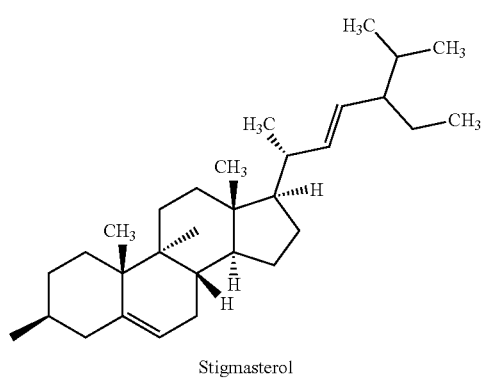

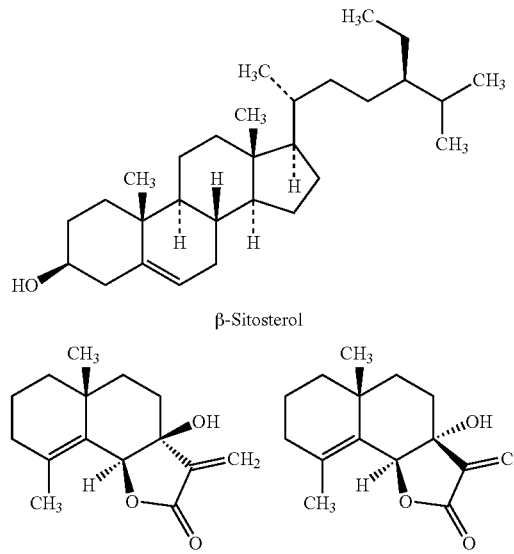

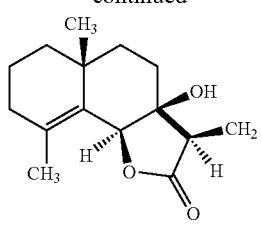
Hydroxy lactones (15-17)
(19)
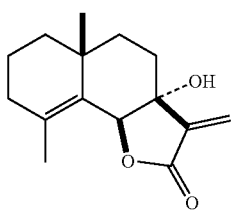
7α-Hydroxyeudesm-4-en-6,12-olide
(20)
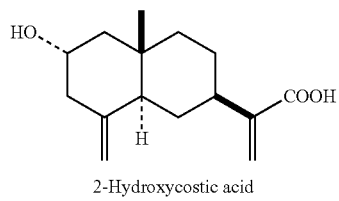
2-Hydroxycostic acid
(21)
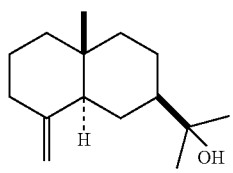
β-Eudesmol
(22)
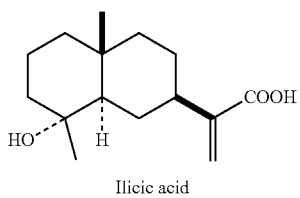
Ilicic acid
(18)
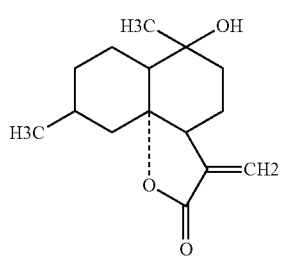
Sesquiterpene lactone
(24)
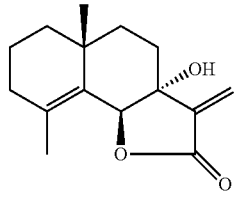
7-Hydroxyfrullanolide
(25)
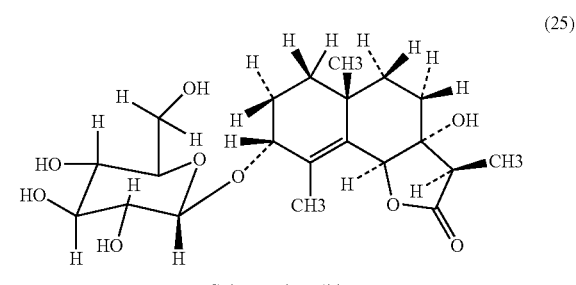
Sphaeranthanolide
(26)
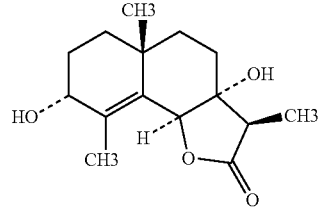
11α-13-dihydro-3α,7α-dihydroxyfrullanolide
(27)
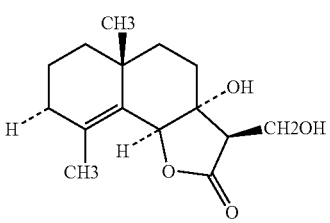
11α-13-dihydro-7α,13α-dihydroxyfrullanolide
(28)
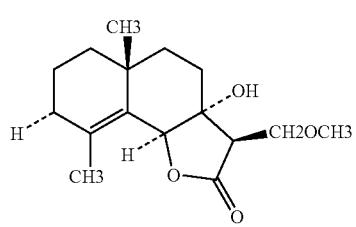
11α-13-dihydro-7α-hydroxy-13-methoxy frullanolide

(29)
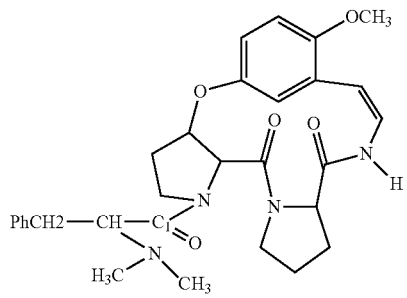
Peptide alkaloid
(30)
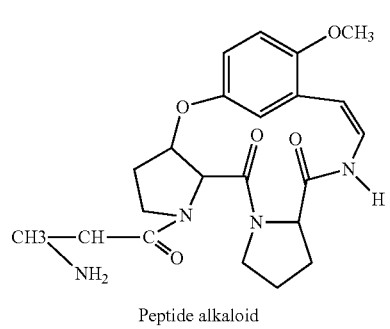
Peptide alkaloid
(31)
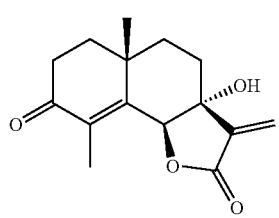
Eudesmanolides
(32)
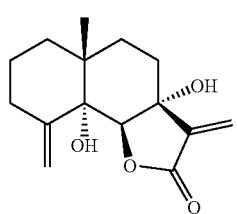
Eudesmanolides
(33)
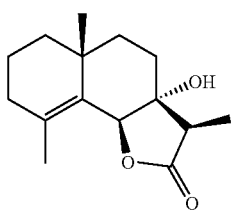
7α-Hydroxyeudesm-4-en-6,12-olide
(34)
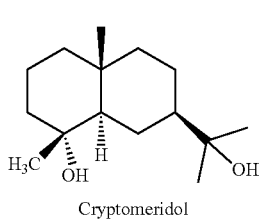
Cryptomeridol
(35)
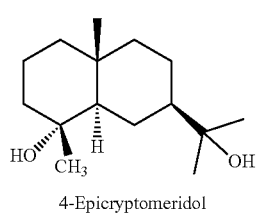
4-Epicryptomeridol
(36)
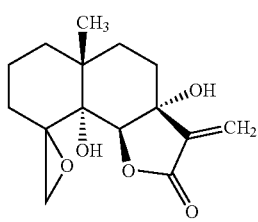
5α,7-Dihydroxyeudesmanolide
(38)
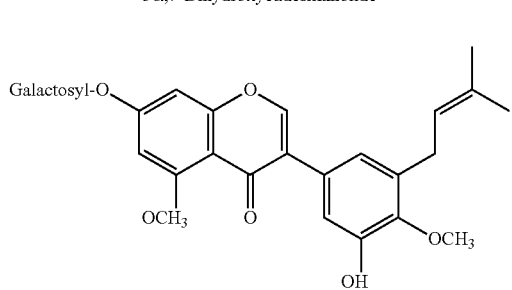
5,4'-Dimethoxy-3'-prenhlbiochanin-7-O-β-D-galactoside
(39)
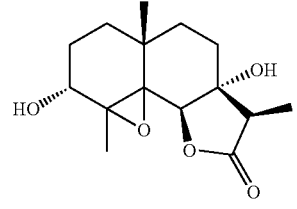
11α-13-Dihydro-3α,7α-dihydroxy-4,5-eposy-6β,7-eudesmanolide
(40)
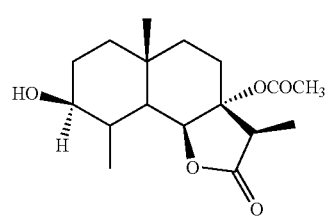
11α-13-Dihydro-7α-acetoxy-3β-hydroxy-6β,7-eudesm-4-enolide

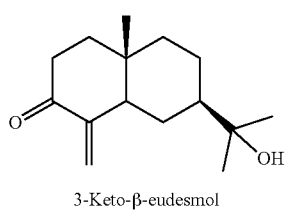
3-Keto-β-eudesmol (41)
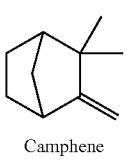
Camphene (42)
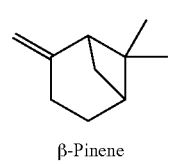
β-Pinene (43)
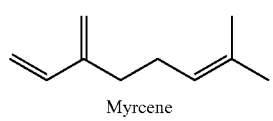
Myrcene (44)
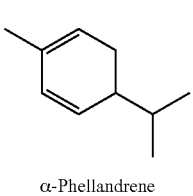
α-Phellandrene (45)
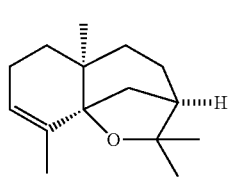
α-Agarofuran (46)
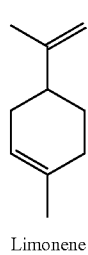
Limonene (47)
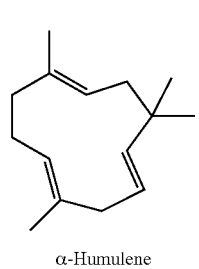
α-Humulene (48)
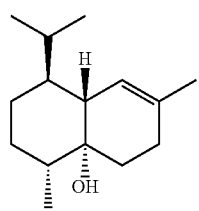
Cubenol (49)
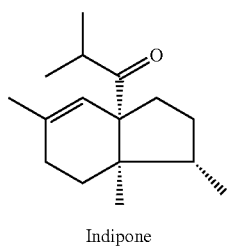
Indipone (50)
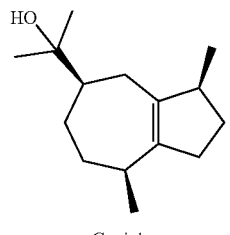
Guaiol (51)
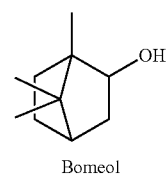
Borneol (52)
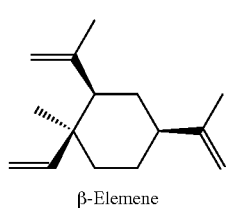
β-Elemene (53)
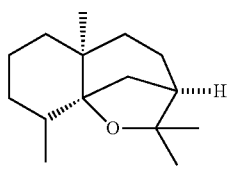
Dihydroagarofuran (54)
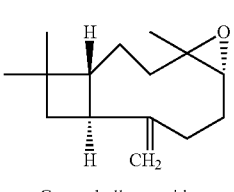
Caryophyllene oxide (55)

-continued (56)

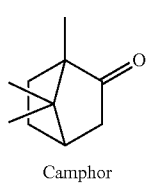

Camphor (57)

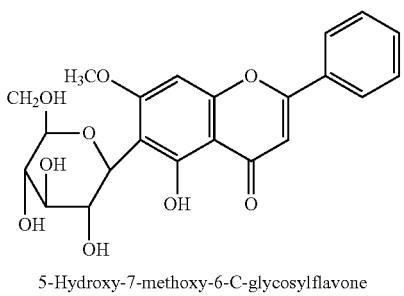

5-Hydroxy-7-methoxy-6-C-glycosylflavone

In some embodiments (for example, when the non-reducing disaccharide is trehalose or a mixture comprising trehalose; optionally in such examples, one or more amino acids are provided, such as one or more of glycine and arginine) the bioactive herbaceous extract may be a secondary metabolite known to have a role in plant defence against insects and pathogens. In other embodiments, the bioactive herbaceous extract may be a nutrient useful to human or animal health. In some embodiments the bioactive herbaceous extract is an extract from *Sphaeranthus indicus*, for example quercetin.

In some embodiments (for example, when the non-reducing disaccharide is trehalose or a mixture comprising trehalose; optionally in such examples, one or more amino acids are provided, such as one or more of glycine and arginine) the bioactive herbaceous extract is a compound as described herein which is normally unstable in an aqueous solution, for example having a half-life of less than 10, 20 or 30 hours in physiological saline solution.

It has been found that bioactive herbaceous extracts (for example, a *Sphaeranthus indicus* extract, such as an extract comprising quercetin, a *cannabis* plant extract, such as an extract comprising one or more cannabinoids, an olive tree extract, or a citrus tree extract) are especially well stabilized when the silicon particle is contacted with at least one non-reducing disaccharide, for example, a non-reducing disaccharide selected from sucrose, trehalose, raffinose, stachyose and verbascose, in particular trehalose, or mixtures containing trehalose.

Further Components

In certain embodiments of all aspects of the invention (for example, when the non-reducing disaccharide is trehalose or a mixture comprising trehalose; optionally in such examples, one or more amino acids are provided, such as one or more of glycine and arginine) the composition further comprises loading the silicon particles with a charged bioactive herbaceous extract. In certain embodiments of all aspect of the invention, the silicon particles are loaded with a cationic bioactive herbaceous extract. In another aspect of all embodiments of the invention, the silicon particles are loaded with an anionic bioactive herbaceous extract.

The composition of the invention (for example, a composition wherein the non-reducing disaccharide is trehalose or a mixture comprising trehalose; optionally in such examples, one or more amino acids are provided in the composition, such as one or more of glycine and arginine) preferably further comprises one or more bioactive herbaceous extract active pharmaceutical ingredients (API), for example each API may be present at up to 0.01%, 0.05%, 0.1%, 0.5%, 1%, 2%, 4%, 6%, 8%, 10%, 15%, 20%, or 25% by weight of the total composition.

The bioactive herbaceous extract (for example, a *Sphaeranthus indicus* extract, such as an extract comprising quercetin, a *cannabis* plant extract, such as an extract comprising one or more cannabinoids, an olive tree extract, or a citrus tree extract) is preferably located in association with the silicon particles.

The second aspect of the invention provides a composition of the invention (for example, a composition wherein the non-reducing disaccharide is trehalose or a mixture comprising trehalose; optionally in such compositions, an amino acid may be provided, such as one or more of arginine and glycine) and one or more further ingredients. Whilst those further ingredients normally include one or more excipients, they may also optionally include one or more further bioactive agents.

The compositions according to the invention include those suitable for oral, parenteral (including subcutaneous, intradermal, intramuscular, intravenous, and intra-articular), inhalation (including fine particle dusts or mists which may be generated by means of various types of metered dose pressurized aerosols, nebulizers or insufflators), rectal and topical (including dermal, transdermal, transmucosal, buccal, sublingual, and intraocular) administration, although the most suitable route may depend upon, for example, the condition and disorder of the recipient.

The compositions may conveniently be presented in unit dosage form and may be prepared by any of the methods well known in the field of formulation. All methods include the step of bringing the active ingredient into association with the carrier which constitutes one or more accessory ingredients. In general the compositions are prepared by uniformly and intimately bringing into association the silicon nanoparticles with liquid carriers or finely divided solid carriers or both and then, if necessary, shaping the product into the desired formulation.

Compositions of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2S, 1988, the contents of which are incorporated herein by reference.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. Moulded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxypropyl cellulose (HPC), hydroxypropyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Compositions for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilised) condition requiring only the addition of the sterile liquid carrier, for example saline or water-for-injection, immediately prior to use.

Exemplary compositions for parenteral administration include injectable suspensions of the composition of the invention which can further contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremophor. An aqueous carrier may be, for example, an isotonic buffer solution at a pH of from about 3.0 to about 8.0, preferably at a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition preferably does not include oxidizing agents and other compounds that are known to be deleterious to any active ingredient. Excipients that can be included are, for instance, proteins, such as human serum albumin or plasma preparations. If desired, compositions may also contain minor amounts of non-toxic auxiliary substances, such as wetting or emulsifying agents, preservatives, and pH buffering agents and the like, for example sodium acetate or sorbitan monolaurate.

Exemplary compositions for nasal aerosol or inhalation administration include solutions in saline, which can contain, for example, benzyl alcohol or other suitable preservatives, absorption promoters to enhance bioavailability, and/or other solubilizing or dispersing agents such as those known in the art. Conveniently in compositions for nasal aerosol or inhalation administration the composition of the invention may be delivered in a suitable powder inhaler. Capsules and cartridges of e.g., gelatin for use in such an inhaler can be formulated to contain a powder mix of the compound and a suitable powder base, for example lactose or starch.

Compositions for rectal administration may be presented as a retention enema or a suppository with the usual carriers such as cocoa butter, synthetic glyceride esters or polyethylene glycol. Such carriers are typically solid at ordinary temperatures, but liquefy and/or dissolve in the rectal cavity to release the drug.

Compositions for topical administration in the mouth, for example buccally or sublingually, include lozenges comprising the active ingredient in a flavoured base such as sucrose and acacia or tragacanth, and pastilles comprising the active ingredient in a basis such as gelatin and glycerine or sucrose and acacia. Exemplary compositions for topical administration include a topical carrier such as Plastibase (mineral oil gelled with polyethylene).

According to some embodiments a pharmaceutical composition of the invention is a unit dosage composition containing a single effective dose, or an appropriate fraction thereof, of the bioactive herbaceous extract.

It should be understood that in addition to the ingredients particularly mentioned above, the compositions of this invention may include other agents conventional in the art having regard to the type of composition in question, for example those suitable for oral administration may include flavouring agents.

The composition of the invention may also be suitably administered as sustained release systems. Suitable examples of sustained release systems of the invention include suitable polymeric materials, for example semi permeable polymer matrices in the form of shaped articles, e.g., films, or microcapsules; suitable hydrophobic materials, for example as an emulsion in an acceptable oil; or ion exchange resins; and sparingly soluble derivatives of the compound of the invention, for example, a sparingly soluble salt. Sustained release systems may be administered orally; rectally; parenterally; intracisternally; intravaginally; intraperitoneally; topically, for example as a powder, ointment, gel, drop or transdermal patch; buccally; sublingually or as an oral or nasal spray.

A therapeutically effective amount of a bioactive herbaceous extract or a cosmetically effective amount of a bioactive herbaceous extract may be administered as a single pulse dose, as a bolus dose, or as pulse doses administered over time, for example during the course of a day, during the course of a week, or during the course of a month.

In many preferred embodiments, the composition of the invention is a topical cream or gel, for example it may comprise a pharmaceutically compatible or a cosmetically compatible cream or gel suitable for topical application to the skin or another body surface comprising a cream base into which composition of the invention is suspended.

A pharmaceutically or cosmetically compatible cream comprises a cream base. Cream bases are typically emulsions of water in oil or oil in water. Preferably, they are oil in water emulsions where the oil phase contains a mixture of lipids, sterols and emollients.

A pharmaceutically or cosmetically compatible gel comprises the composition of the invention dispersed in the liquid phase of the gel. The gel is preferably a hydrogel (colloidal gel) comprising cross-linked polymers such as polyethylene oxide, polyacrylamides or agarose, methylcellulose, hyaluronan, elastin-like polypeptide, carbomer (polyacrylic acid), gelatin or collagen.

A composition of the invention may be in the form of an adhesive patch comprising a backing layer and an adhesive film wherein the adhesive film comprises the composition according to the invention or a cream or gel comprising the composition according to the invention.

A patch according to the invention is typically a transdermal patch and consists of a backing layer, which may be textile, polymer or paper and protects the patch from the outer environment; optionally a membrane, for example a polymer membrane which prevents migration of the fluorouracil through the backing layer; and an adhesive. The composition of the invention may be provided in the adhesive layer or in a reservoir of the patch or a gel may act as a reservoir within the patch product (a so-called "monolithic" device).

A patch can be useful in ensuring the correct dosage of a subject by decreasing the likelihood of incautious or inappropriate use by the final user. Moreover, a patch will limit the area treated, avoiding inadvertent spreading to other areas.

According to a third aspect of the invention, there is provided the composition of the invention (for example, a composition wherein the non-reducing disaccharide is trehalose, or a mixture comprising trehalose; optionally an amino acid may be provided in such compositions, such as one or more of arginine and glycine) for use as a medicament.

Optionally, the medicament may be used in treating a subject in need of a bioactive herbaceous extract included in the composition of the invention.

For example if the composition of the invention includes an anti-inflammatory drug the medicament may be for use in treating or preventing inflammation, injury or pain.

If the composition of the invention includes an immunosuppressive agent, the medicament may be for use in treating or preventing hypersensitivity, allergy, transplanted organ rejection, hayfever, pet allergy, allergic rhinitis or urticarial.

If the composition of the invention includes an analgesic or antipyretic, the medicament may be used for treating or preventing pain or fever.

If the composition of the invention includes an anti-fungal agent, the medicament may be used for treating or preventing a fungal infection, for example Candidiasis, cryptococcal meningitis, athletes foot, jock-itch or fungal nail infection.

If the composition of the invention includes an anti-viral compound, the medicament may be used for treating or preventing a viral infection.

If the composition of the invention includes an antiparasitic compound, the medicament may be used for treating or preventing a parasitic infection or infestation.

If the composition of the invention includes an antibacterial compound such as an antibiotic, the medicament may be used for treating or preventing a bacterial infection.

If the composition of the invention includes an antineoplastic compound, the medicament may be used for treating or preventing a neoplastic condition such as cancer, in particular it may be used for treating a cancer of the skin or other body surface to which the product of the invention may be topically applied.

If the composition of the invention includes an anaesthetic, the medicament may be used for inducing or sustaining a state of anaesthesia in a subject.

If the composition of the invention includes a muscle relaxant, the medicament may be used for providing muscle relaxation in a subject, for example as a treatment for a spastic condition, a condition characterised by spasms, or for use as pre-medication prior to surgery.

If the composition of the invention includes an antihypertensive agent, the medicament may be used for treating or preventing hypertension.

If the composition of the invention includes an anti-anxiety agent, the medicament may be used for treating or preventing anxiety.

If the composition of the invention includes a hormone, the medicament may be used to treat or prevent a condition caused by hormone deficiency such as a menopausal disorder, or diabetes, a growth disorder, hypogonadism, a thyroid disorder, or osteoporosis.

If the composition of the invention includes a contraceptive agent, the medicament may be used to prevent pregnancy.

If the composition of the invention includes an antidepressant, the medicament may be used to treat or prevent depression.

If the composition of the invention includes an antiepileptic agent, the medicament may be used to treat or prevent epilepsy.

If the composition of the invention includes a somnulant, the medicament may be used to treat or prevent insomnia.

If the composition of the invention includes an antiemetic, the medicament may be used to treat or prevent nausea and/or vomiting.

If the composition of the invention included an antipsychotic compound, the medicament may be used to treat or prevent psychosis.

If the composition of the invention includes a spermicidal compound, the medicament may be used as a spermicide, optionally in combination with a barrier contraceptive device.

If the composition of the invention includes an erectile dysfunction (ED) drug, the medicament may be used to treat or prevent erectile dysfunction and/or male impotence.

If the composition of the invention includes an ocular lubricant the medicament may be used to treat or prevent a dry eye condition.

If the composition of the invention includes a laxative, the medicament may be used to treat or prevent constipation.

If the composition of the invention includes a bile acid sequestrant or a bowel bulking agent or a serotonin agonist, the medicament may be used to treat or prevent diarrhoea.

If the composition of the invention includes an appetite suppressant, the medicament may be used to treat or prevent obesity.

According to a fourth aspect of the invention, there is provided a method of treating a medical condition comprising administering an effective dose of one or more bioactive herbaceous extracts (for example, one or more of a *Sphaeranthus indicus* extract, such as an extract comprising quercetin, a *cannabis* plant extract, such as an extract comprising one or more cannabinoids, an olive tree extract, or a citrus tree extract) to a subject in need thereof, wherein the bioactive herbaceous extracts are administered as a pharmaceutical composition according to an embodiment of the second aspect of the invention (for example, a composition wherein the non-reducing disaccharide is trehalose or a mixture comprising trehalose; optionally in such compositions, an amino acid is provided such as one or more of arginine and glycine).

According to certain preferred embodiments of the fourth aspect of the invention, the medical condition is one of the medical conditions referred to above in reference to the third aspect of the invention, and the bioactive herbaceous extract is optionally one of the pharmaceutically active agents referred to above in the context of treating or preventing a particular condition.

According to a fifth aspect of the invention there is provided a method of providing a cosmetic benefit to a subject comprising administering to said subject a composition prepared according to the first aspect of the invention or a composition according to the second aspect of the invention.

A method according to the fifth aspect of the invention may optionally provide a cosmetic benefit selected from skin hydration, skin softening, a reduction in the appearance of skin aging, a reduction in the appearance of age related skin spots, a reduction in unevenness of skin tone, skin whitening, a reduction in the prominence of scars, a reduction of skin redness, or a reduction in the appearance of skin surface capillaries. Such a method preferably involves the administration of a topical composition of the invention to the skin.

Methods of the fifth aspect of the invention also include methods that provide a cosmetic benefit to the hair, nails and eye lashes. Such methods may optionally involve the administration to the subject of a composition which is, respectively, a shampoo or hair conditioner or tonic; a nail varnish or cream; or a mascara.

According to the sixth aspect of the invention there is provided a method of protecting a plant (for example, a *Cannabis sativa* plant) comprising administering to said plant a composition according to an embodiment of the second aspect of the invention, wherein the bioactive herbaceous extract comprises a plant protection compound, for example an insecticide, an insect repellent or a plant nutrient (for example, a *Sphaeranthus indicus* extract; the bioactive herbaceous extract may comprise quercetin). Such methods include protecting a plant from a viral, fungal or bacterial disease, or protecting a plant from oxidative stress.

In nature, phenolic compounds are involved in plant defence, for example during infection. For example, it may be an antifungal phytoalexin, isoflavanoid, pterocarpan, furocoumarin, flavan, stilbene or phenanthrene compound.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

Preparation of Silicon Particles

The silicon particles relating to the invention may conveniently be prepared by techniques conventional in the art, for example by milling processes or by other known techniques for particle size reduction. They may be silicon-containing particles made from sodium silicate particles, colloidal silica or silicon wafer materials. Macro, micro, or nano scale particles are ground in a ball mill, a planetary ball mill, plasma or laser ablation methods or other size reducing mechanism. The resulting particles may be air classified to recover particles of the required size. It is also possible to use plasma methods and laser ablation for particle production.

Porous particles may be prepared by methods conventional in the art, including the methods described herein.

Preparation of Creams and Gels

Creams and gels may be formulated simply by dispersing (i.e. mixing) the silicon particles of the invention with a cream or gel base. For example, the silicon particles may be stirred into a pharmaceutical cream base. In respect of a gel, the powder may be stirred into the gel matrix in powder form and then the gel hydrated, or it may be stirred into a pre-hydrated gel.

Preparation of Patches

A patch may be formulated by any appropriate method, for example, a patch containing a muco-adhesive hydrophilic gel may be produced. The gel may be produced with silicon nanoparticles of the invention dispersed in it, and the gel may optionally be dried by gentle evaporation of water to become a film with the required adhesive properties.

Preparation of Silicon-Based Matrix Intended for Stabilizing Herbal Extracts

In the preparation of solid silicon mesoporous nanoparticles (previously described in patent US Patent 2012/0128786 A1), according to the present invention the various substances are used in the following proportions:

a) non-reducing disaccharide such as trehalose present as 0.1 to 10%, preferably from 0.5 to 8% by weight of the total final dried powder;

b) the amount of herbal extract ranges from 0.001 to 25% by weight of the total final dried powder;

c) the amount of substances suitable to sterically stabilize the microparticles ranges from 0.01 to 2.5% by weight with respect to total dried powder weight;

d) the amount of electron charge-stabilizer ranging from 0.1 to 2.5% by weight of the total final dried powder;

e) in order to preserve the pore structure and long-range pore ordering of such functionalized silicon particles, the number of functional groups incorporated by any method shouldn't exceed 25 percent of surface coverage due to the difference in condensation rates between the herbaceous extract and silica precursors. The efficiency of loading depends on the nature of the organic functional groups.

f) Such final product can be used for human/animal medical products and supplements, by mixing the obtained microparticles powder within aqueous and/or oily final formulations, as described in US Patent 2012/0128786 A1.

g) Such final product can be used for botanical application. The final product can be administered as a powder or aqueous formulation such as an aqueous suspension, for administering plant supplements as well as specific herbaceous extract molecules with proved antibiotic and antiviral activity against plant pathogens, aphids, and parasites. Such a final product is intended as a product able to be administered to specific parts of the plant to be treated, i.e. leaves and/or xylematic vessels, as well as soil.

h) Such compositions can be used for botanical administration for improving expression of specific plant metabolites.

The present invention provides, with respect to the prior art processes, the possibility to maintain the bioactive herbaceous extract of choice in a stable state with an appreciable improvement of both bioavailability and half-life of the bioactive herbaceous extract or any derivative thereof in aqueous environments, before and after their administration.

Method 1

This method uses silicon nanoparticles for stabilizing *Sphaeranthus indicus* herbaceous extract in aqueous environments.
1. Weigh 0.1 g of powdered herbaceous extract and place it into a beaker
2. Add 75 ml of distilled water (room temperature) to the powdered herbaceous extract.
3. Magnetically stir the solution for 10 minutes. Due to the presence of woody residue and ash, an insoluble residue will be observed after stirring.
4. Filter the solution using a Whatman filter paper, a funnel and a beaker for collecting the filtrate.
5. The resulting filtrate will appear transparent and yellow-brown in colour.
6. Add 0.0075 g of activated silicon nanoparticle powder (100 nm) (particles are activated by washing in methanol which is then removed by evaporation) to this filtered solution (1% w/v of the overall volume) and
7. Add 0.075 g of trehalose to this filtered solution (10% w/v of the overall volume).
8. Sonicate the obtained solution for 10 minutes.

The obtained aqueous solution is stable for 15 days.

Method 2

This method uses silicon nanoparticles for stabilizing *Sphaeranthus indicus* herbaceous extract in aqueous environments. The stabilized extract is then coated with a lipidic shell.
1. Grind herbaceous plant material to produce powdered material.
2. Weigh 0.1 g of the powdered herbaceous extract into a beaker.
3. Add 75 ml of distilled water (room temperature) to the powdered herbaceous extract.
4. Magnetically stir the solution for 10 minutes. Due to the presence of woody residue and ash, an insoluble residue will be observed after stirring
5. Filter the above solution using a filter paper, a funnel and a beaker for collecting the filtrate.
6. The resulting filtrate will appear transparent and yellow-brown in colour.
7. Add 0.0075 g of activated silicon powder (activation carried out as in method 1) to the filtered solution (1% w/v of the overall volume) and
8. Add 0.075 g of trehalose to this filtered solution (10% w/v of the overall volume).
9. Add to the activated silicon powder in aqueous solution, 4 mg of arginine and 2 mg of glycine.
10. Solubilize 16 mg of lecithin in an organic solvent mixture [$CHCl_3:CH_3OH$, 4:1]
11. Pour the lecithin solution into a round-bottom flask, and remove the solvent using a rotary evaporator to form a lecithin coating.
12. Rehydrate the produced lecithin coating using the aqueous solution containing the herbaceous extract, activated silicon powder, trehalose, arginine and glycine—shake the component using vortex and leave it in the fridge for 3 hours, then move to the freezer for ~4 hours at (−25° C.).
13. Freeze-dry overnight to a dry powder by evaporating the solvent.
14. Rehydrate dried powder in water.

Preparation of Plant Protection Products

Plant protection compounds may be applied as powder, solutions or suspensions (for example aqueous solutions or suspensions or as a dry powder and may be conveniently formulated as such.

Examples

Example 1: Preparation of Silicon Particles and their Activation

Single-side polished P-type or N-type silicon wafers were purchased from Si-Mat, Germany. All cleaning and etching reagents were clean room grade. A heavily doped P Op type Si(100) wafer with a resistivity of 0.005 V $cm^{-1}$ was used as the substrate. A 200-nm layer of silicon nitride was deposited by a low-pressure chemical vapour deposition system. Standard photolithography was used to pattern using an EVG 620 contact aligner. Porous nanoparticles were formed in a mixture of hydrofluoric acid (HF) and ethanol (3:7 v/v) by applying a current density of 80 mA $cm^{-2}$ for 25 s. A high-porosity layer was formed by applying a current density of 320 mA $cm^{-2}$ for 6 s in a 49% HF:ethanol mixture with a ratio of 2:5 (v/v). Smaller pores can be formed in a mixture of HF (49%) and ethanol (3:7 v/v) by applying a current density of 80 mA $cm^{-2}$ for 25 s. In the specific case, pores were formed in a mixture of HF (49%) and ethanol (1:1 v/v) by applying a current density of 6 mA $cm^{-2}$ for 1.75 min. After removing the nitride layer by HF, particles were released by ultrasound in isopropyl alcohol for 1 min. The shape, which is mainly hemispherical, is determined by means of scanning electron micrograph (SEM). The size of pores can be determined by means of nitrogen adsorption-desorption volumetric isotherms. After etching, the samples were rinsed with pure ethanol and dried under a stream of dry high-purity nitrogen prior to use.

Etched Silicon wafers, P+ or N− were crushed using a ball mill and/or pestle & mortar. The fine powder sieved using Retsch branded sieve gauge 38 μm and shaker AS200. Uniformity at the selected sizes (20-100 μm) is achieved by the aperture size of the sieve. The particle sizes were measured by the Quantachrome system and PCS from Malvern Instruments. Samples were kept in the closed container until further use.

NanoSilicon powder was also obtained from Sigma and Hefel Kaier, China. The particle size measured by PCS and recorded (size was range between 20-100 nm) before subjected to the loading and etching. Silicon wafers were crushed using a ball mill, or using mortar and pestle. The fine powder was sieved using a Retsch branded sieve gauge 38 μm and shaker AS200 and uniform nanoparticles of the desired size were collected.

Activation of Silicon Nanoparticles 250 mL of ethanol and 500 mg of 30 nm diameter porous silicon nanoparticles were mixed and stirred for 30 minutes. The solution was then centrifuged for 30 minutes at 3000 rpm. The supernatant was discarded and the nanoparticles washed in 5 ml of distilled water and transferred to a round bottomed flask. The contents of the flask were frozen (2 hours at −25° C.). The frozen nanoparticles were freeze-dried using a freeze dryer overnight. The resultant dry powder is the activated silicon nanoparticles.

Example 2: Characterization of *Sphaeranthus indicus* Herbaceous Extract

An extract of *Sphaeranthus Indicus*, whole plant powder (Dr Wakde's Natural Health Care, London) was purchased as Gorakhmundi herb. The stated composition was 28% total ash, 7% acid insoluble ash, 3% alcohol soluble extractive, 12% water soluble extractive. It is a light brown powder with a characteristic odour.

Example 3: Solubility of *Sphaeranthus indicus* Herbaceous Extract

Powder as described above was weighed and dispersed in different solvents in order to determine the maximum solubility of the herbaceous extract. The study was carried out at 20° C. and the initial powder concentration in each solvent was 1 mg/ml. Solvents used were distilled water, methanol, ethanol and chloroform.

Results

At a concentration equal to 1 mg/ml, the herbaceous extract showed incomplete solubility in all solvents. It is assumed that this is due to the acid insoluble ash fraction of the herbaceous extract and/or some woody residue.

Example 4: Aqueous Extractions of *Sphaeranthus indicus* Powder

In order to obtain a clear solution, 0.1 g of dry powder was dissolved in 75 ml of distilled water at 75° C. The solution was filtered using filter paper. A second solution was obtained by further extraction of the solid residue using distilled water at 20° C., and again that solution was filtered using filter paper.

A UV-Vis light absorption analysis was carried out at wavelengths of 190 to 800 nm using distilled water as the zeroing blank. To avoid saturating the instrument the solutions were diluted 1:10 in distilled water.

UV-Vis analysis was performed using a Shimadzu spectrophotometer UV-1800, with a computer integrated apparatus (Software UV-Probe) and a quartz cuvette: Quart Suprasil Hellma 10*2 mm, and double beam activation mode.

Results

The filtered solutions both appeared clear with a yellowish colour. FIG. 1 shows the appearance of *Sphaeranthus indicus* herbal powder and the hot water extracted solution and the used filtration paper.

Figure 3:
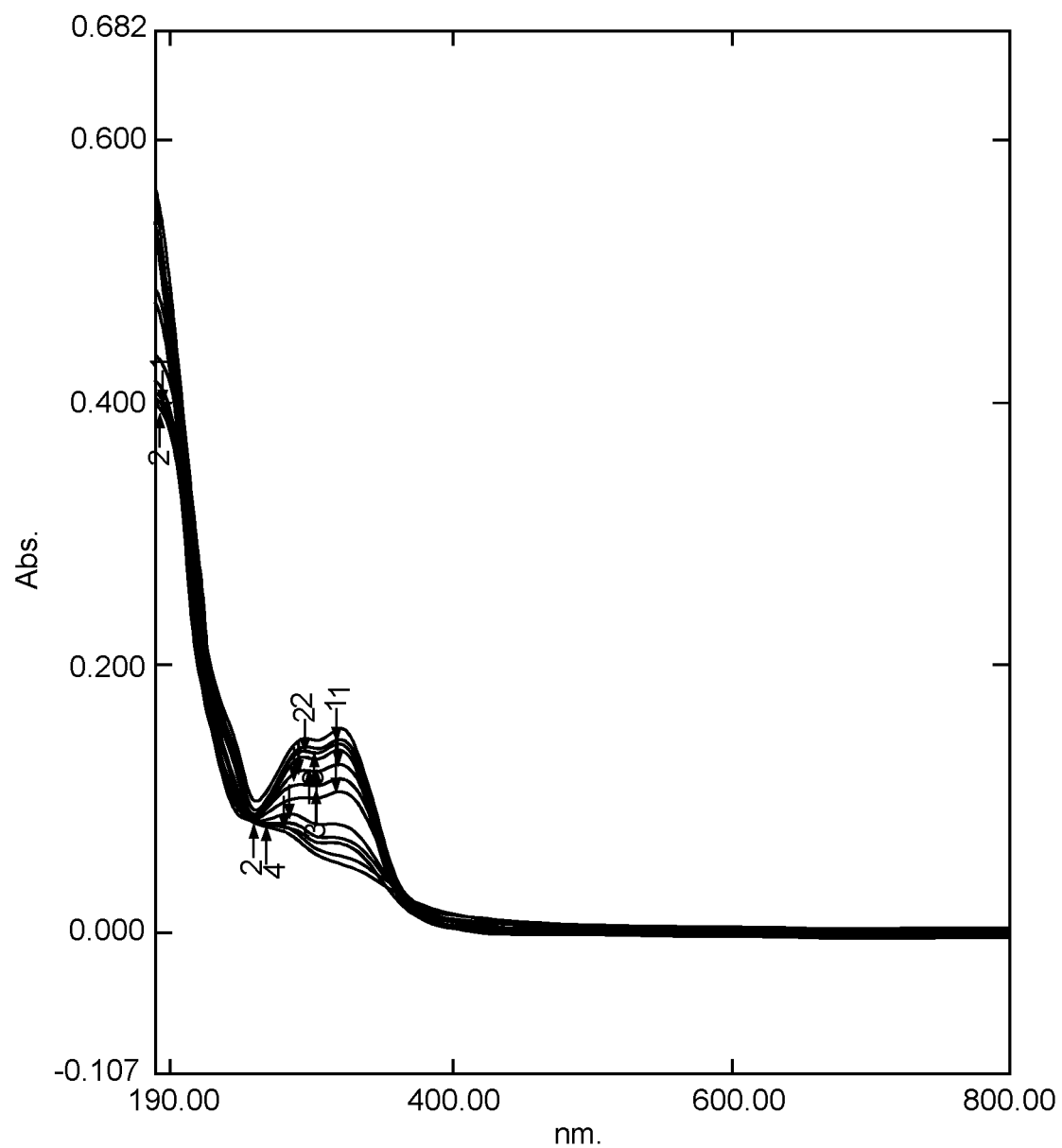
FIG. 3. UV-Vis absorption analysis of *Sphaeranthus indicus* filtered hot water over time. The graph shows the alteration of the maximum detectable absorbance over a period of 24 hours. The individual labels cannot be seen but there are peaks at 322 nm, 263 nm and 195 nm. The lower lines are recorded at a later time point than the upper lines.

The results of light absorption analysis are shown in FIG. 3 which is an overlay of spectra obtained every 30 minutes following extraction. Peaks of absorption can be seen at 322 nm, 263 nm and 195 nm. The peak intensity diminished with time. This indicates that the solution is unstable because the concentration of compounds responsible for the peaks decline over less than 24 hours at room temperature.

Because the individual spectra cannot be easily distinguished in FIG. 3, the data for 0 and 24 hours is presented in tabular form below.

| Time of analysis | Peaks | Wavelength, nm | Absorbance |
|---|---|---|---|
| 0 hours | 1 | 322.5 | 0.147 |
| | 2 | 263.5 | 0.084 |
| | 3 | 195.5 | over 1 |
| 24 hours | 1 | 322.5 | Not appreciable |
| | 2 | 263.5 | Not appreciable |
| | 3 | 195.5 | 0.385 |

Discussion

Although the dry powder of the herbaceous extract appears to show reasonable stability in solid form, in solution the compounds in *Sphaeranthus indicus* extract show very poor stability. This is thought to be due to rapid oxidation. Similar results are found with other herbaceous extracts. Whilst oxidation in solution is a problem with many compounds, it is a problem which is especially problematic which herbaceous extracts because they tend to contain high levels of compounds such as phenols and the other preferred compounds disclosed herein, which have evolved to oxidize easily in the environment as part of the plant's defence mechanism against damage. This limits the usefulness of such phytochemicals in medical, plant protection, cosmetic and other applications because, in those applications, solvent-carried formations are often necessary or preferred, but can rapidly be rendered useless by degradation.

Example 5: Enhancing *Sphaeranthus indicus* Extract Stability

This experiment demonstrates that *Sphaeranthus indicus* extract can be stabilized in an aqueous environment using silicon particles in accordance with the invention which have been treated with the non-reducing disaccharide trehalose.

Activated silicon particles having a 100 nm nominal diameter were prepared in accordance with the protocol of Example 1.

Solutions of *Sphaeranthus indicus* extract were treated with trehalose, activated silicon particles or both trehalose and activated silicon particles in accordance with methods 2 and 3.

The prepared samples were analysed for light absorption using a UV-Vis spectrophotometer as described in the above examples before and after being suspended for 24 hours in distilled water. As a comparison, freshly obtained but untreated extract was also analysed.

Results

A summary of the results is shown in the table below:
(THR=trehalose, Sph ind=*Sphaeranthus indicus* extract)

| Sample | lambda max, nm | Abs |
|---|---|---|
| Sph ind in THR dil 1-10 in water; time = 0 hrs | 323.50 | 0.150 |
| Sph ind in THR dil 1-10 in water; time = 24 hrs | 322.50 | 0.129 |
| Sph ind in activated silicon dil 1-10 in water; time = 0 hrs | 324.00 | 0.130 |
| Sph ind in activated silicon dil 1-10 in water; time = 24 hrs | 322.00 | 0.100 |
| Sph ind in activated silicon + THR, dil 1-10 in water; time = 0 hrs | 324.00 | 0.135 |
| Sph ind in activated silicon + THR, dil 1-10 in water; time = 24 hrs | 322.00 | 0.122 |
| Sph ind dil 1-10 in water; time = 0 hrs | 322.50 | 0.127 |
| Sph ind dil 1-10 in water; time = 24 hrs | No peak | N/A |

As can be seen from the data in the table, untreated *Sphaeranthus indicus* extract is completely degraded after 24 hours in distilled water. This observed poor stability confirms the results seen in previous examples.

Treatment with trehalose and/or activated silicon particles showed enhanced stability with relatively little change observed in absorbance peak position (lambda max) or height of that peak (Abs). This is evidence for stabilisation of the compounds in the extract by trehalose and by activated silicon particles in accordance with the invention. The most complete stabilisation, as evidenced by the lowest changes in absorption spectra, were observed in the extract treated with a combination of activated silicon particles and trehalose.

Figure 4:
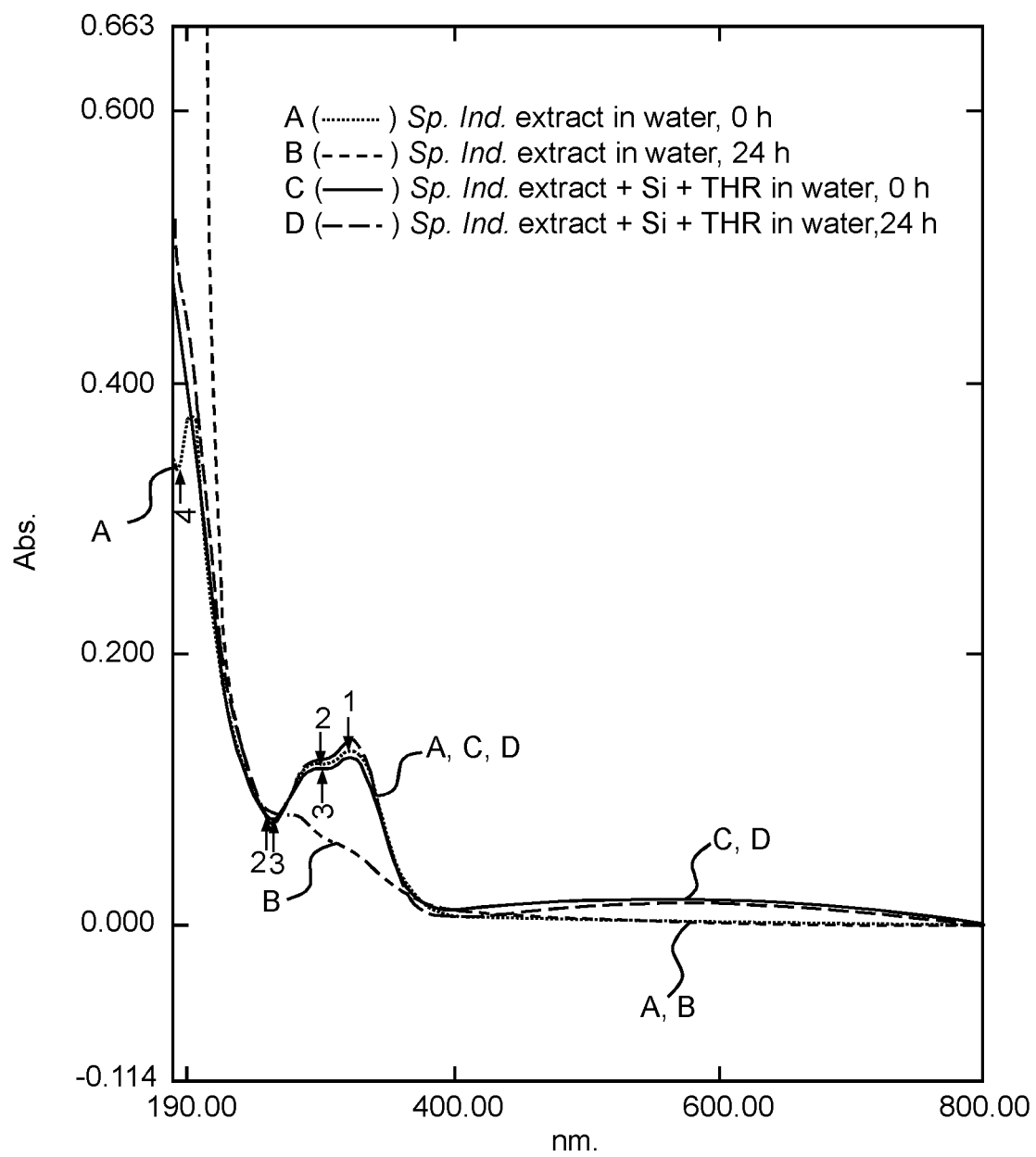
FIG. 4. UV-Vis absorbance spectra showing as line A (orange in original) *Sphaeranthus indicus* herbaceous extract in water at 0 hrs; as line B (red in original) *Sphaeranthus indicus* herbaceous extract in water at 24 hrs; as line C (green in original) *Sphaeranthus indicus* herbaceous extract stabilized with silicon particles and trehalose in water at 0 hrs; and as line D (blue in original) *Sphaeranthus indicus* herbaceous extract stabilized with silicon particles and trehalose in water at 24 hrs.

FIG. 4 shows this data as full spectra. It can be seen that the peaks between 200 nm and 400 nm are present in fresh extract (line A) and in extract stabilized with activated silicon particles and trehalose (line C=0 hr; line D=24 hrs), but that in unstabilized extract this peak is absent after 24 hours (line B).

Figure 5:
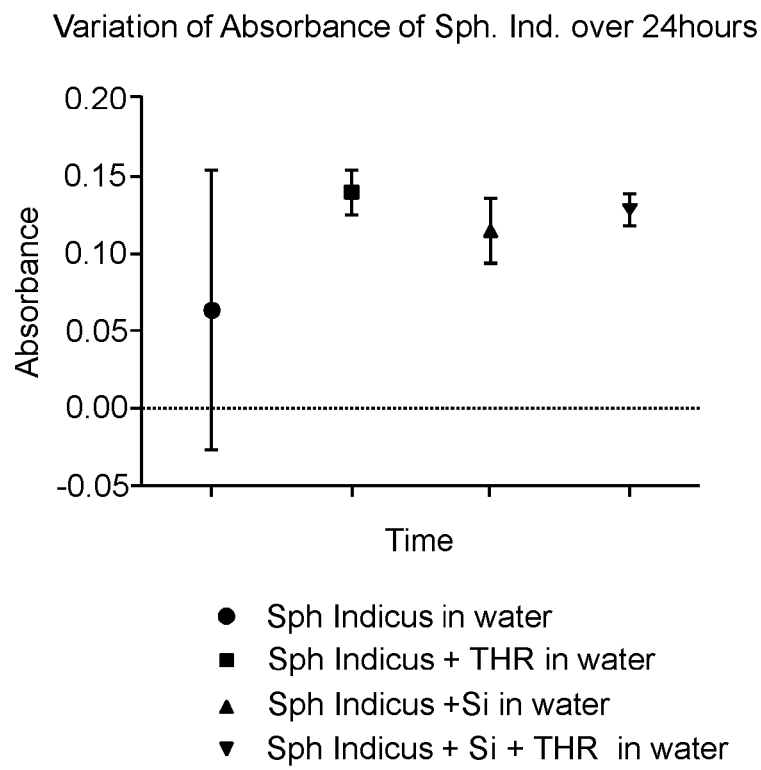
FIG. 5. Graph showing variation of absorbance of *Sphaeranthus indicus* extract over 24 hours. Graphical deviation represents variation of absorbance from time=0 hours to time=24 hours. Only *Sphaeranthus indicus* extract in water showed a significant susceptibility to degradation (circles). The same extract treated with trehalose only (square) or silicon only (upright triangle) showed a certain stability over the same time period of analysis. A synergism between trehalose and silicon powder in stabilizing the extract in water is also seen (inverted triangle).

FIG. 5 shows the difference (loss) of absorbance graphically between 0 hr and 24 hr for each sample. It can be seen that activated silicon particles and trehalose are both capable of imparting stability to the herbaceous extract, but that the greatest stability is seen in samples which were stabilized with both agents.

Example 6: Extract Stability Over 15 Days

Example 5 was repeated over a 15 day period with the absorbance of each sample recorded at 0, 24, 96, 254 and 350 hours.

Results

A summary of the data obtained is provided in the table below.

| Sample | Lambda 1, nm | Abs 1 | Lambda 2, nm | Abs 2 |
|---|---|---|---|---|
| Sph Ind. Trehalose 0 hrs | 323.500 | 0.150 | 297.000 | 0.137 |
| Sph Ind. Trehalose 24 hrs | 322.500 | 0.129 | 297.500 | 0.119 |
| Sph Ind. Trehalose 96 hrs | 321.500 | 0.126 | 294.000 | 0.119 |
| Sph Ind. Trehalose 254 hrs | 319.000 | 0.136 | 290.000 | 0.138 |
| Sph Ind. Trehalose 350 hrs | 319.000 | 0.139 | 287.500 | 0.153 |
| Sph Ind. silicon particles 0 hrs | 324.000 | 0.130 | 293.000 | 0.121 |
| Sph Ind. silicon particles 24 hrs | 322.000 | 0.100 | 293.000 | 0.092 |
| Sph Ind. silicon particles 96 hrs | 322.000 | 0.098 | 293.000 | 0.090 |
| Sph Ind. silicon particles 254 hrs | 320.000 | 0.098 | 292.000 | 0.095 |

-continued

| Sample | Lambda 1, nm | Abs 1 | Lambda 2, nm | Abs 2 |
|---|---|---|---|---|
| Sph Ind. silicon particles 350 hrs | 323.000 | 0.086 | 288.000 | 0.095 |
| Sph Ind. silicon particles + Trehalose 0 hrs | 324.000 | 0.135 | 293.000 | 0.121 |
| Sph Ind. silicon particles + Trehalose 24 hrs | 322.000 | 0.122 | 295.000 | 0.113 |
| Sph Ind. silicon particles + Trehalose 96 hrs | 323.000 | 0.116 | 293.000 | 0.108 |
| Sph Ind. silicon particles + Trehalose 254 hrs | 321.000 | 0.118 | 291.000 | 0.116 |
| Sph Ind. silicon particles + Trehalose 350 hrs | 321.000 | 0.129 | 287.000 | 0.142 |

It can be seen that, in respect of the "lambda 1" peak (approximately 319 to 325 nm) all samples show at least some stability as indicated by relatively low absorbance changes. The greatest stability is seen with extracts treated with both activated silicon particles and trehalose. In respect of the "lambda 2" peak (approximately 287 to 298 nm) there is also relatively good stability. The increase in absorption with time at the "lambda 2" wavelength is hypothesised to be due to changes in molecular equilibria between eudesmandide and glycosyl species.

The 15-days period of analysis highlighted that the sum of the overall chemical species contributing to the final herbal extract UV-Vis absorbance spectra tend to generate real, but not substantial, alteration of reciprocal peaks of interest over time. This might be indicative of an equilibrium of interested species in the aforementioned solution. This result would be in line with previously published data on *Sphaeranthus indicus* analysis. [Emani L R, Ravada S R, Garaga M R, Meka B, Golakoti T. Four new Sesquiterpenoids from *Sphaeranthus indicus*. Nat Prod Res. 2017 Nov. 31(21):2497-2504. doi: 10.1080/14786419.2017.1315576. Epub 2017 Apr. 17].

It has been demonstrated that *Sphaeranthus indicus* extract contains the following chemical species of interest: eudesmanolides, sesquiterpenoids, sesquiterpene lactones, sesquiterpene acids, flavone glycosides, flavonoid C-glycosides, isoflavone glycosides, sterols, sterol glycosides, alkaloids, peptide alkaloids, amino acids and sugars [Ramachandran S. Review on *Sphaeranthus indicus* Linn. (Ko tt aikkarantai). Pharmacogn Rev. 2013 July; 7(14):157-69. doi: 10.4103/0973-7847.120517.

Eudesmanolides are of interest due to their susceptibility to generate Glycosyl derivatives, as shown below:

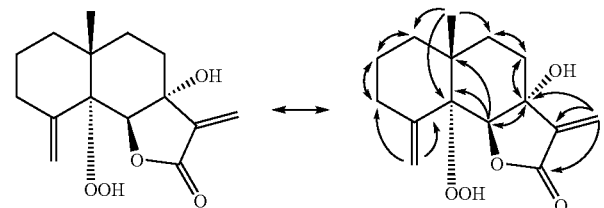
5α-hydroperoxy-7α-hydroxy-isosphaerantholide

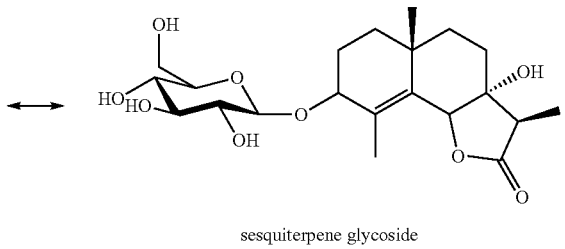
sesquiterpene glycoside

It is reasonable to believe that alterations of UV peaks over time could be due to equilibria between different species in aqueous environments. The reciprocal total amount of species and related glycosyl derivatives, together with the specific UV absorbance of single species, might contribute to the variation of UV-Vis absorbance spectra over time.

No other significant alteration of the UV-Vis absorbance spectra was observed over the analyzed period, neither had any significant absorbance been recorded in the absorbance range of 300-550 nm. This is consistent with the absence of significant oxidation of those chemical species that contribute to generate the overall UV-Vis spectrum.

Figure 6:
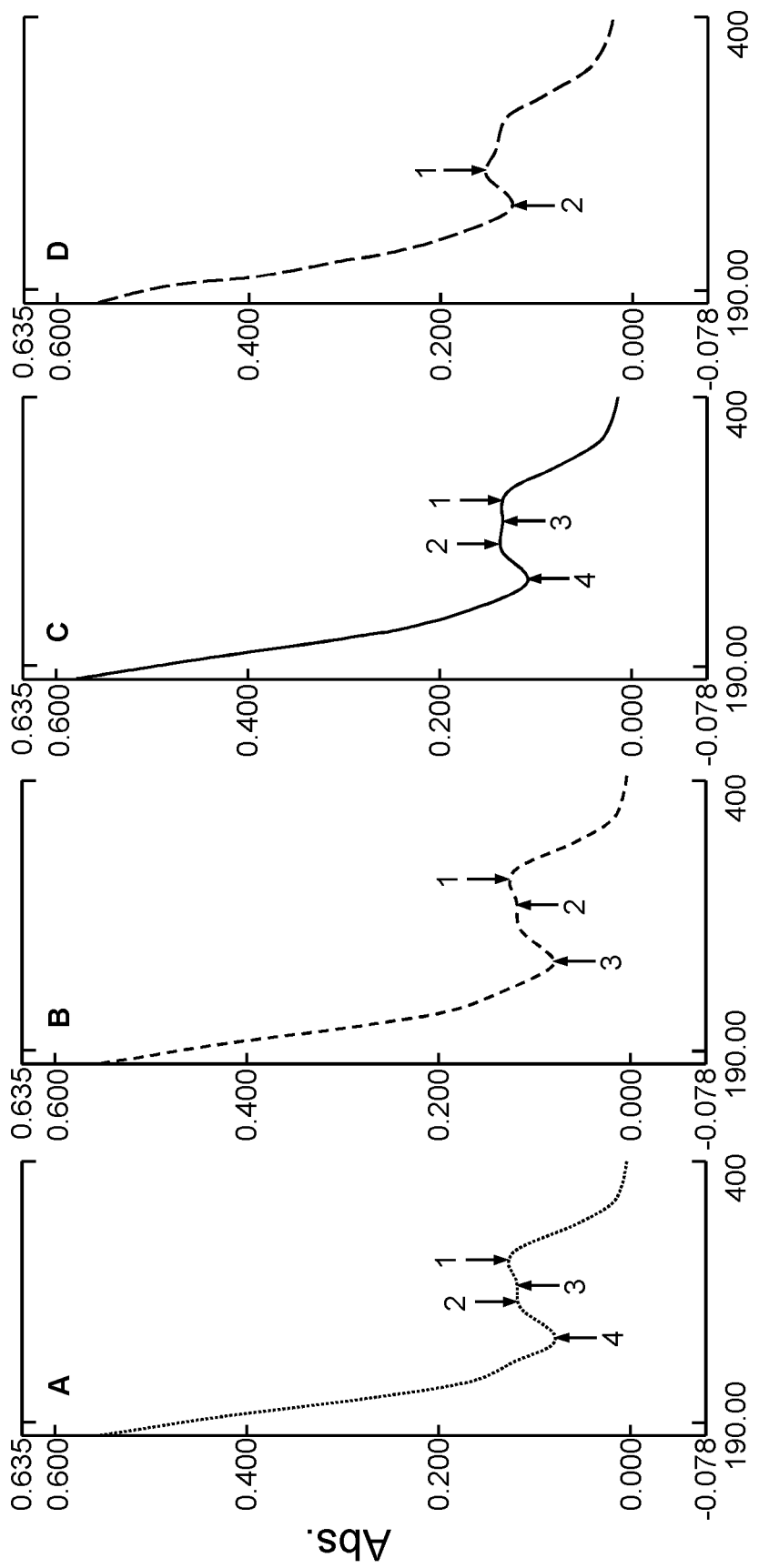
FIG. 6. *Sphaeranthus indicus* stabilized in trehalose: UV-Vis spectra at 24 hrs (A), 96 hrs (B), 254 hrs (C) and 350 hrs (D).
Figure 7:
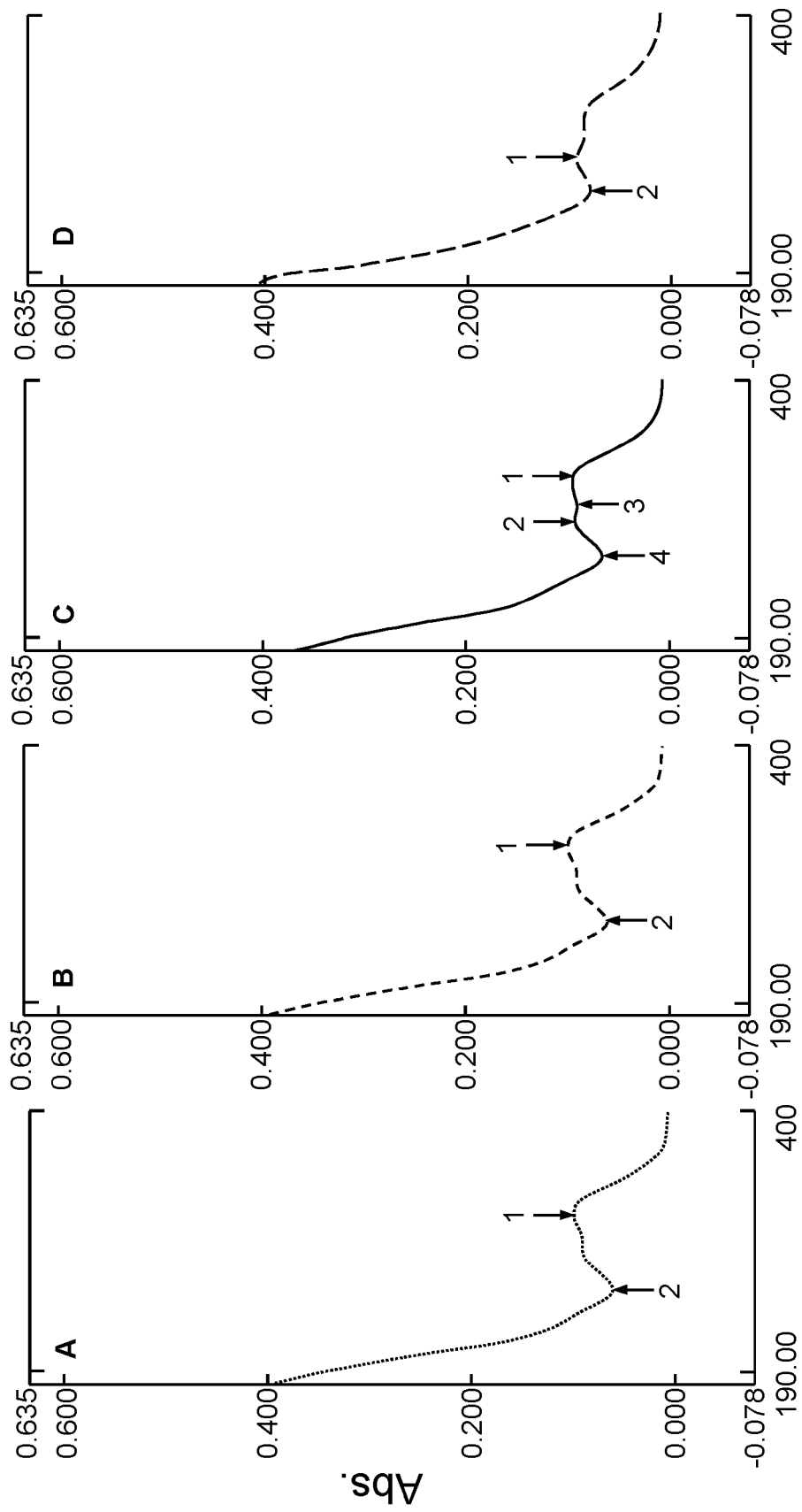
FIG. 7. *Sphaeranthus indicus* stabilized with activated silicon particles: UV-Vis spectra at 24 hrs (A), 96 hrs (B), 254 hrs (C) and 350 hrs (D).
Figure 8:
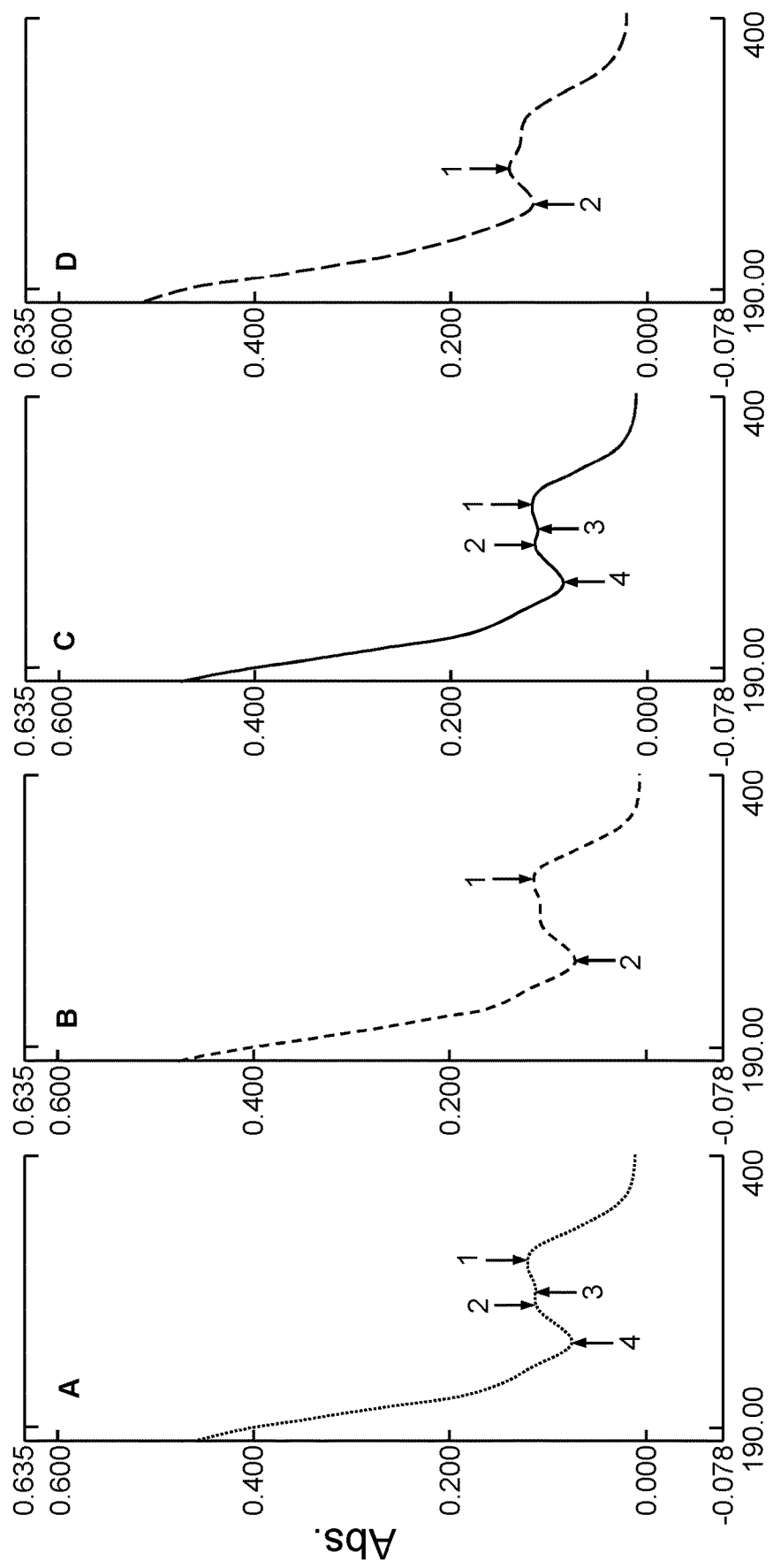
FIG. 8. *Sphaeranthus indicus* stabilized with activated silicon particles and trehalose: UV-Vis spectra at 24 hrs (A), 96 hrs (B), 254 hrs (C) and 350 hrs (D).

FIGS. 6, 7, and 8 show, respectively, the complete spectra for the three stabilized compositions and demonstrate that changes are minimal and there is generally good stability of the extract over 15 days.

The raw absorbance data is provided in the table below and shown graphically as FIG. 9.

| Raw data | S. Ind + Si | S. Ind + THR | S. Ind + Si + THR |
|---|---|---|---|
| Number of values | 5 | 5 | 5 |
| Minimum | 0.0860 | 0.1260 | 0.1160 |
| 25% Percentile | 0.0920 | 0.1275 | 0.1170 |
| Median | 0.0980 | 0.1360 | 0.1220 |
| 75% Percentile | 0.1150 | 0.1445 | 0.1320 |
| Maximum | 0.1300 | 0.1500 | 0.1350 |
| Mean | 0.1024 | 0.1360 | 0.1240 |
| Std. Deviation | 0.01640 | 0.009407 | 0.007906 |
| Std. Error of Mean | 0.007332 | 0.004207 | 0.003536 |
| Lower 95% CI of mean | 0.08204 | 0.1243 | 0.1142 |
| Upper 95% CI of mean | 0.1228 | 0.1477 | 0.1338 |
| Sum | 0.5120 | 0.6800 | 0.6200 |

Figure 9:
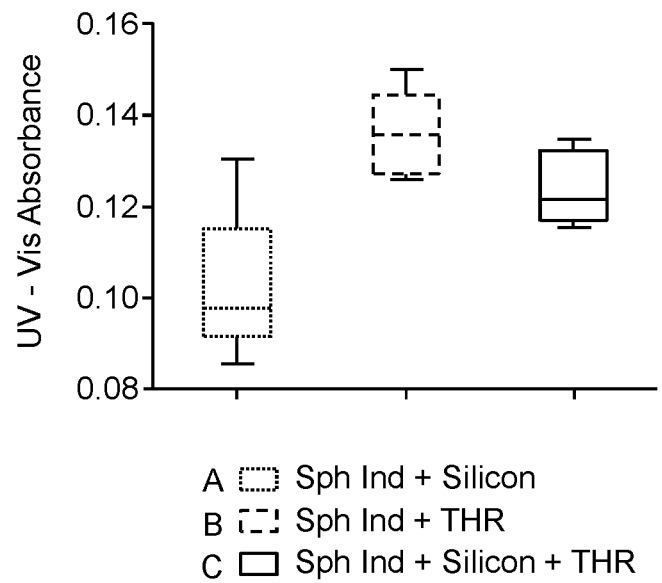
FIG. 9. Shows graphically the variation of absorbance spectra for *Sphaeranthus indicus* extract at 350 hrs for different methods of stabilization.

THR = trehalose,
S Ind. = *Sphaeranthus indicus*,
Si = activated silicon particles As can be seen in FIG. 9, the lowest variation in absorbance over time (i.e., the best stability) is seen in extracts stabilized with both activated silicon particles and trehalose (plot C).

While trehalose has been demonstrated to enhance stability of APIs for agricultural and human application, the combination of silicon and trehalose of the present invention demonstrates surprisingly high levels of stability. In particular the combination of trehalose and silicon particles create an environment which increases the stability of herbaceous extracts when they are suspended in aqueous media.

It is hypothesised that the combination of non-reducing disaccharide and silicon enhances the stability of APIs in aqueous environment by limiting access of water molecules to the API once it is physical absorbed to silicon surface, due to the direct interaction of trehalose with mild polar entities, i.e. water molecules themselves. Such interactions have the potential to result in associations between silicon, trehalose,—the API and water molecules.

Example 7: Reversing Oxidative Stress on *Cannabis sativa* Plants Using Nanoparticle-Stabilised Quercetin Samples were prepared comprising silicon nanoparticles and (in varying amounts) the bioactive herbaceous extract quercetin, the non-reducing disaccharide trehalose, the lipid lecithin and the amino acids arginine and glycine. The delivery system of the invention is capable of stabilising quercetin (such as quercetin extracted from *Sphaeranthus indicus*) under conditions such as ambient and/or aqueous conditions, such as in vivo conditions. These samples were prepared in a similar manner to the samples of earlier Examples. The composition of the samples is indicated in the table below.

| | Delivery system | | | Quercetin | | | |
|---|---|---|---|---|---|---|---|
| Sample | Si-NP | Lecithin | Arginine:Glycine | Quercetin | Trehalose | Total volume | % in final formulation |
| GS1 | 4 mg | 16 mg | 4 mg: 2 mg | 2.5 mg | 4 mg | 50 mL | 0.05 |
| GS2 | 4 mg | 0 | 4 mg: 2 mg | 2.5 mg | 4 mg | 50 mL | 0.05 |
| GS3 | 4 mg | 16 mg | 0 | 2.5 mg | 4 mg | 50 mL | 0.05 |
| GS4 | 4 mg | 0 | 0 | 2.5 mg | 4 mg | 50 mL | 0.05 |
| GS5 | 0 | 0 | 0 | 2.5 mg | 0 | 50 mL | 0.05 |
| GS6 | 4 mg | 0 | 0 | 0 | 4 mg | 50 mL | 0 |
| GS7 | 0 | 0 | 0 | 0 | 0 | 50 mL | 0 |

These samples were applied to the leaves of *Cannabis sativa* plants under controlled conditions, with salt being used to impose conditions of stress on the leaves.

Figure 10:
FIG. 10. Photographs showing: salt-exposed *Cannabis sativa* plants sprayed with buffer solution (labelled Buffer NaCl); salt-exposed *Cannabis sativa* plants sprayed with the delivery system of the invention alone (labelled Platform NaCl); and *Cannabis sativa* plants sprayed with the delivery system carrying quercetin (two formulations, labelled SiSaf1 NaCl and SiSaf2 NaCl respectively). Each treated plant is shown standing next to a control salt-exposed *Cannabis sativa* plant (to which no treatment was applied) labelled Control NaCl. The original colour photographs shows visible browning of leaves treated with buffer only and control leaves, compared to leaves treated with the delivery system, particularly compared to leaves treated with the delivery system carrying quercetin. The photographs show visible wilting of leaves treated with buffer only and control leaves, compared to leaves treated with the delivery system, particularly compared to leaves treated with the delivery system carrying quercetin.

Samples containing the silicon nanoparticle delivery system of the invention (silicon nanoparticles, trehalose and optionally one or more of lecithin and the amino acids arginine and glycine) showed a protective effect on the *Cannabis sativa* leaves subjected to salt stress, compared to a control sample (GS7) without the delivery system. Samples containing the delivery system of the invention and quercetin also showed a protective effect on the *Cannabis sativa* leaves subjected to salt stress. This protective effect included a visible reduction in wilting and browning of the *Cannabis sativa* leaves, compared to the control sample (GS7), see FIG. 10.

Leaves treated with samples GS1 and GS2 had a statistically significant ($p<0.05$) decrease in expression of marker genes involved in stress response (ERF1, Gibb REC and HSP70-2) compared to control plants sprayed with buffer (GS7) or quercetin alone (GS5).

The leaves of plants treated with the delivery system of the invention alone or with quercetin had a statistically significant higher % leaf moisture content, compared to control plants sprayed with buffer (GS7) or quercetin alone (GS5).

It is apparent that the formulation of the present invention is capable of protecting crops, such as *Cannabis sativa* plants, from oxidative stress. This is achieved by delivering both orthosilicic acid and a stabilised bioactive herbaceous extract to plant cells in a controlled and sustained manner. Delivery of the bioactive herbaceous extract to plant cells over time is achieved via stabilisation of the bioactive herbaceous extract using the silicon nanoparticle delivery system of the present invention.

The invention claimed is:

1. A method for stabilizing a hydrophilic bioactive herbaceous extract in a composition comprising silicon nanoparticles, the nanoparticles containing at least 50% by weight silicon, and having an average diameter of between 10 and 1000 nm, the method comprising bringing the hydrophilic bioactive herbaceous extract into contact with the silicon nanoparticles, in the presence of trehalose, wherein the silicon nanoparticles and trehalose act in synergy to stabilize the hydrophilic bioactive herbaceous extract, and wherein the hydrophilic bioactive herbaceous extract is an anionic molecule or a cationic molecule and is selected from a *Sphaeranthus indicus* extract, a *cannabis* plant extract, an olive tree extract, and a citrus tree extract.

2. The method according to claim 1, wherein trehalose is present at a ratio by weight to silicon of at least 1:10.

3. The method according to claim 1, wherein the silicon nanoparticles are additionally brought into contact with the bioactive herbaceous extract in the presence of at least one amino acid, optionally wherein the ratio of amino acid to silicon is from 0.05:1 to 2:1.

4. The method according to claim 3, wherein the at least one amino acid is selected from aspartic acid, glutamic acid, tyrosine, glycine, alanine, valine, leucine, isoleucine, proline, phenylalanine, methionine, tryptophan, histidine, threonine, asparagine, arginine, and glutamine; and/or wherein the bioactive herbaceous extract is selected from a phenol, a diphenol, a polyphenol, a terpene, a hemiterpene, a monoterpene, an irridoid, a sesquiterpene, a diterpene, a sesterterpene, a triterpene, a steroid, a tetraterpene, a norisoprenoid, a flavonoid, a flavanol, or a flavanone.

5. The method according to claim 1, wherein the silicon nanoparticles are porous.

6. The method according to claim 1, wherein the bioactive herbaceous extract is quercetin.

7. The method according to claim 1, wherein the herbaceous extract is susceptible to degradation on exposure to oxygen or other oxidants.

8. The method according to claim 1, wherein the herbaceous extract contains one or more flavonoid compounds and polyphenols.

9. The method according to claim 1, wherein the herbaceous extract is a secondary metabolite known to have a role in plant defense against insects and pathogens.

10. The method according to claim 1, wherein the herbaceous extract is a compound having a half-life of less than 10 hours in physiological saline solution.

11. The method according to claim 1, wherein the silicon nanoparticles have an average diameter of between 20 nm and 400 nm.

12. A composition for stabilizing a hydrophilic bioactive herbaceous extract, the composition comprising silicon nanoparticles, the nanoparticles containing at least 50% by weight silicon, and having an average diameter of between 10 and 1000 nm and trehalose, and a bioactive herbaceous extract, wherein the trehalose is present at a ratio by weight to silicon of at least 1:10; wherein the silicon nanoparticles and trehalose are arranged to stabilize the hydrophilic bioactive herbaceous extract synergistically; and wherein the hydrophilic bioactive herbaceous extract is an anionic molecule or a cationic molecule and is selected from a *Sphaeranthus indicus* extract, a *cannabis* plant extract, an olive tree extract, and a citrus tree extract.

13. The composition according to claim 12, further comprising at least one amino acid, optionally wherein the ratio of amino acid to silicon is from 0.1:1 to 2:1.

14. The composition according to claim 13, wherein the at least one amino acid is selected from aspartic acid, glutamic acid, tyrosine, glycine, alanine, valine, leucine, isoleucine, proline, phenylalanine, methionine, tryptophan, histidine, threonine, asparagine, or glutamine.

15. The composition according to claim 12, wherein the silicon nanoparticles are porous.

16. The composition according claim 12, wherein the composition is an aqueous composition, containing at least 10, 20, or 50% water by weight, or wherein the composition is a powder for dispersion in water.

17. A method of protecting a plant from pest damage or treating a fungal, bacterial or parasitic infection of said plant, or of protecting said plant from oxidative stress, comprising administering to said plant a composition according to claim 12.

18. The method according to claim 17, wherein the plant is a *Cannabis sativa* plant, and/or wherein the bioactive herbaceous extract comprises quercetin.

\* \* \* \* \*